United States Patent
Marsala et al.

(10) Patent No.: US 10,688,285 B2
(45) Date of Patent: Jun. 23, 2020

(54) SPINAL SUBPIAL GENE DELIVERY SYSTEM

(71) Applicant: THE REGENTS OF THE UNIVERSITY OF CALIFORNIA, Oakland, CA (US)

(72) Inventors: Martin Marsala, Solana Beach, CA (US); Atsushi Miyanohara, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 56 days.

(21) Appl. No.: 15/790,477

(22) Filed: Oct. 23, 2017

(65) Prior Publication Data

US 2018/0117282 A1     May 3, 2018

Related U.S. Application Data

(63) Continuation-in-part of application No. 15/544,973, filed as application No. PCT/US2015/065704 on Dec. 15, 2015.

(60) Provisional application No. 62/110,340, filed on Jan. 30, 2015, provisional application No. 62/413,267, filed on Oct. 26, 2016.

(51) Int. Cl.
| | |
|---|---|
| *A61M 25/06* | (2006.01) |
| *A61K 9/00* | (2006.01) |
| *A61K 48/00* | (2006.01) |
| *A61P 25/28* | (2006.01) |
| *C12N 7/00* | (2006.01) |
| *A61B 17/34* | (2006.01) |
| *A61P 25/16* | (2006.01) |
| *A61P 25/26* | (2006.01) |
| *C12N 15/86* | (2006.01) |

(52) U.S. Cl.
CPC ....... *A61M 25/065* (2013.01); *A61B 17/3417* (2013.01); *A61K 9/0085* (2013.01); *A61K 48/0058* (2013.01); *A61K 48/0075* (2013.01); *A61P 25/16* (2018.01); *A61P 25/26* (2018.01); *A61P 25/28* (2018.01); *C12N 7/00* (2013.01); *C12N 15/86* (2013.01); *A61B 2017/3454* (2013.01); *A61M 2210/0693* (2013.01); *C12N 2750/14143* (2013.01); *C12N 2750/14171* (2013.01)

(58) Field of Classification Search
CPC .................................................. A61M 25/065
See application file for complete search history.

(56) References Cited

U.S. PATENT DOCUMENTS

| | | | |
|---|---|---|---|
| 8,292,874 B2 | 10/2012 | Stivland et al. | |
| 2002/0082390 A1 | 6/2002 | Friddle et al. | |
| 2003/0130577 A1* | 7/2003 | Purdy | A61B 17/12113 600/433 |
| 2008/0051357 A1 | 2/2008 | Chang et al. | |
| 2013/0211380 A1 | 8/2013 | Aquino et al. | |
| 2014/0058357 A1 | 2/2014 | Keyser et al. | |
| 2014/0073684 A1* | 3/2014 | Stoffel | C12N 15/113 514/44 A |
| 2015/0224331 A1 | 8/2015 | Marsala | |
| 2015/0343038 A1 | 12/2015 | Marsala | |
| 2018/0008727 A1* | 1/2018 | Marsala | C12N 15/86 |
| 2019/0071486 A1 | 3/2019 | Marsala | |

FOREIGN PATENT DOCUMENTS

| | | |
|---|---|---|
| CN | 103328038 A | 9/2013 |
| WO | 1994/10988 A | 5/1994 |
| WO | 2004/060464 A2 | 7/2004 |
| WO | 2010/071832 A1 | 6/2010 |
| WO | 2011/057171 A1 | 5/2011 |
| WO | 2012/075337 A2 | 6/2012 |
| WO | 2014/047540 A1 | 3/2014 |
| WO | 2014/184576 A2 | 11/2014 |
| WO | 2016/122791 A1 | 8/2016 |

OTHER PUBLICATIONS

Poston et a. (Journal of Medical Engineering & Technology. 2011; 35(5): 246-253). (Year: 2011).*
Kantor et al. "Clinical Applications Involving CNS Gene Transfer," Adv Genet., 2014, 87:71-124.
Bouard et al. "Viral vectors: from virology to transgene expression," British Journal of Pharmacology, 2009, 157:153-165.
Adkins et al. "Tiagabine: A Review of its Pharmacodynamic and Pharmacokinetic Properties and Therapeutic Potential in the Management of Epilepsy," Drugs, Mar. 1998, 55(3):437-460.
Gholizadeh et al. "Transduction of the Central Nervous System After Intracerebroventricular Injection of Adeno-Associated Viral Vectors in Neonatal and Juvenile Mice," Human Gene Therapy Methods, Aug. 2013, 24:205-213.
EP14742941 Extended European Search Report dated Jun. 20, 2016.
Dayton et al. "The advent of AAV9 expands applications for brain and spinal cord gene delivery." Expert Opinion on Biological Therapy, Jun. 15, 2012, 12(6):757-766.
Federici et al. "Robust spinal motor neuron transduction following intrathecal delivery of AAV9 in pigs." Gene Therapy, 2012, 19(8):852-859.
Foust et al. "Intravascular AAV9 preferentially targets neonatal neurons and adult astrocytes." Nature Biotechnology, Jan. 2009, 27(1):59-65.
Hirai et al. "Intrathecal shRNA-AAV9 Inhibits Target Protein Expression in the Spinal Cord and Dorsal Root Ganglia of Adult Mice." Human Gene Therapy Methods, Apr. 1, 2012, 23(2):119-127.

(Continued)

*Primary Examiner* — Scott Long
(74) *Attorney, Agent, or Firm* — Wagenknecht IP Law Group, PC

(57) ABSTRACT

Delivery devices, systems, and methods related thereto may be used in humans for spinal delivery of cells, drugs or vectors. Thus, the system enables subpial delivery, which leads to a near complete spinal parenchymal AAV9-mediated gene expression or distribution in both white and grey matter.

22 Claims, 20 Drawing Sheets

(56) References Cited

OTHER PUBLICATIONS

Kakinohana et al. "Combinational Spinal GAD65 Gene Delivery and Systemic GABA-Mimetic Treatment for Modulation of Spasticity." PLOS One, Jan. 2012, 7(1):e30561.
PCT/US2017/024285 International Search Report and Written Opinion dated Aug. 10, 2017.
Jin et al. "Demonstration of Functional Coupling between Gamma-Aminobutyric acid (GABA) Synthesis and Vesicular GABA Transport into Synaptic Vesicles," Proc Natl Acad Sci USA, Apr. 2003, 100(7):4293-4298.
EP15880645 Extended European Search Report dated May 24, 2018.
Colak et al. "Adenovirus-mediated gene therapy for experimental spinal cord tumors: tumoricidal efficacy and functional outcome," Brain Research, May 1995, 691:76-82.
JP2017-540569 Office Action dated Jun. 26, 2018.
JP2017-540569 Office Action dated Jun. 4, 2019.
Poston et al. "Catheter delivery systems for infusions into the cortex," Journal of Medical Engineering & Technology, Jul. 2011, 35(5):246-253.
Bell et al. "Motor Neuron Transduction After Intracisternal Delivery of AAV9 in a Cynomolgus Macaque," Human Gene Therapy Methods, Apr. 2015, 26:43-44.
Duque et al. "Intravenous Administration of Self-complementary AAV9 Enables Transgene Delivery to Adult Motor Neurons," Molecular Therapy, Jul. 2009, 17(7):1187-1196.
Foust et al. "Therapeutic AAV9-mediated Suppression of Mutant SOD1 Slows Disease Progression and Extends Survival in Models of Inherited ALS," Molecular Therapy, Dec. 2013, 21(12):2148-2159.
Gray et al. "Preclinical Differences of Intravascular AAV9 Delivery to Neurons and Glia: A Comparative Study of Adult Mice and Nonhuman Primates," Molecular Therapy, Jun. 2011, 19(6):1058-1069.
Kakinohana et al. "Region-specific cell grafting into cervical and lumbar spinal cord in rat: a qualitative and quantitative stereological study," Experimental Neurology, 2004, 190:122-132.
Meyer et al. "Improving Single Injection CSF Delivery of AAV9-mediated Gene Therapy for SMA: A Dose-response Study in Mice and Nonhuman Primates," Molecular Therapy, Mar. 2015, 23(3):477-487.
Passini et al. "Translational Fidelity of Intrathecal Delivery of Self-Complementary AAV9-Survival Motor Neuron 1 for Spinal Muscular Atrophy," Human Gene Therapy, Jul. 2014, 25:619-630.
Usvald et al. "Analysis of Dosing Regimen and Reproducibility of Intraspinal Grafting of Human Spinal Stem Cells in Immunosuppressed Minipigs," Cell Transplantation, 2010, 19:1103-1122.
Xiao et al. "Production of High-Titer Recombinant Adeno-Associated Virus Vectors in the Absence of Helper Adenovirus," Journal of Virology, Mar. 1998, 72(3):2224-2232.
Xu et al. In Vivo Gene Knockdown in Rat Dorsal Root Ganglia Mediated by Self-Complementary Adeno-Associated Virus Serotype 5 Following Intrathecal Delivery, PLoS One, Mar. 2012, 7(3):e32581.
PCT/US2015/065704 International Search Report dated Feb. 25, 2016.
CN201580078566.9 Office Action dated Sep. 24, 2019.

* cited by examiner

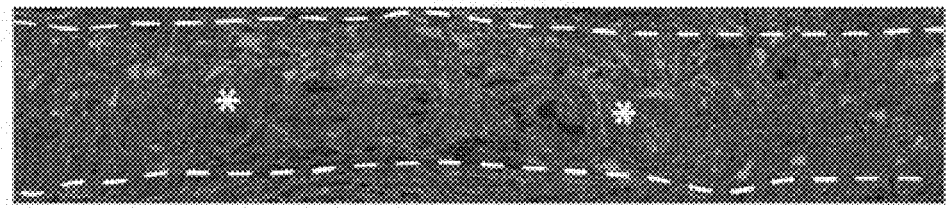
FIG. 3A
FIG. 3B
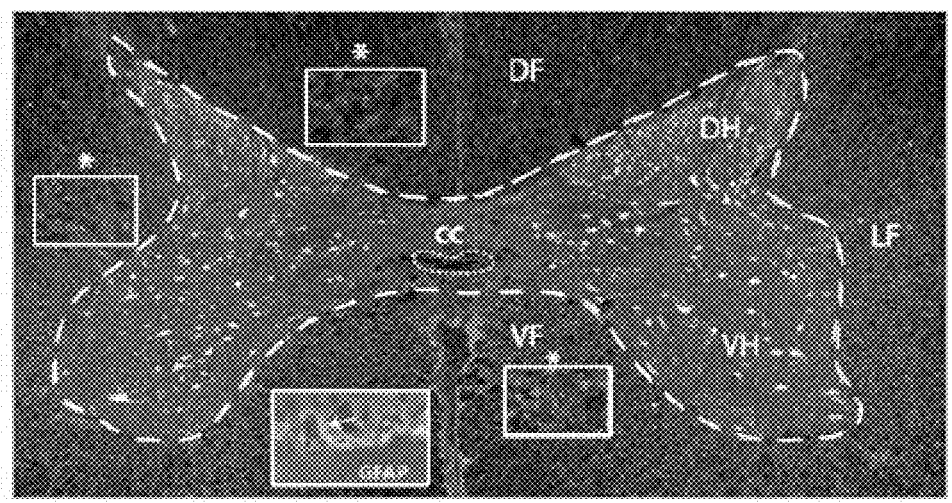
FIG. 3C
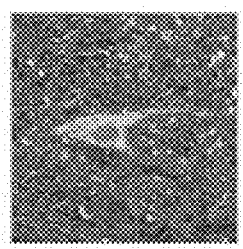 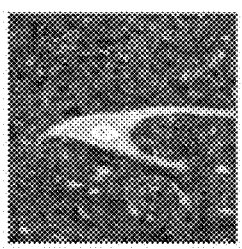  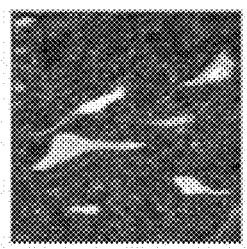
FIG. 3D  FIG. 3E  FIG. 3F  FIG. 3G

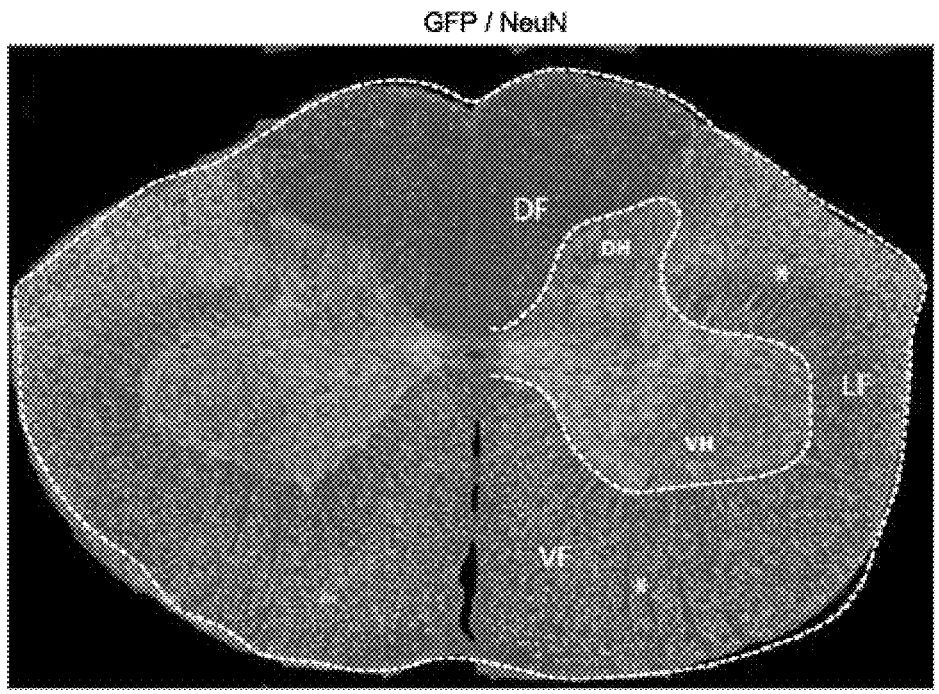
FIG. 4A
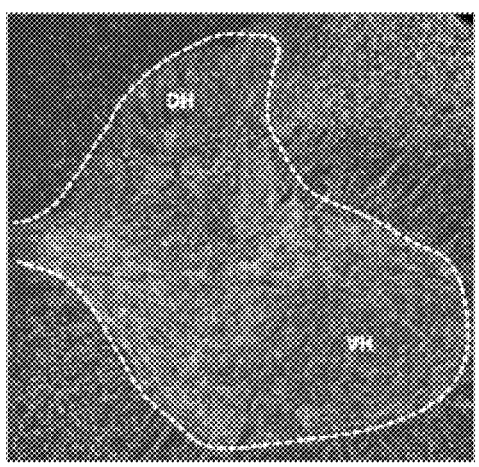 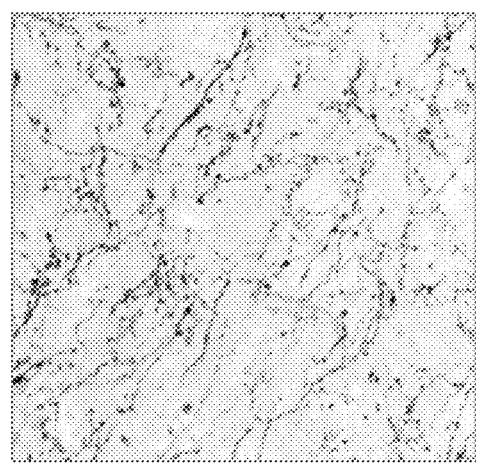
FIG. 4B  FIG. 4C

GFP / DAPI

FIG. 7E   FIG. 7F

Survival and migration of human fetal spinal stem cells at 6 months after Subpial (cervical +lumbar) cell delivery in immunodeficient rat.

upper cervical upper lumbar

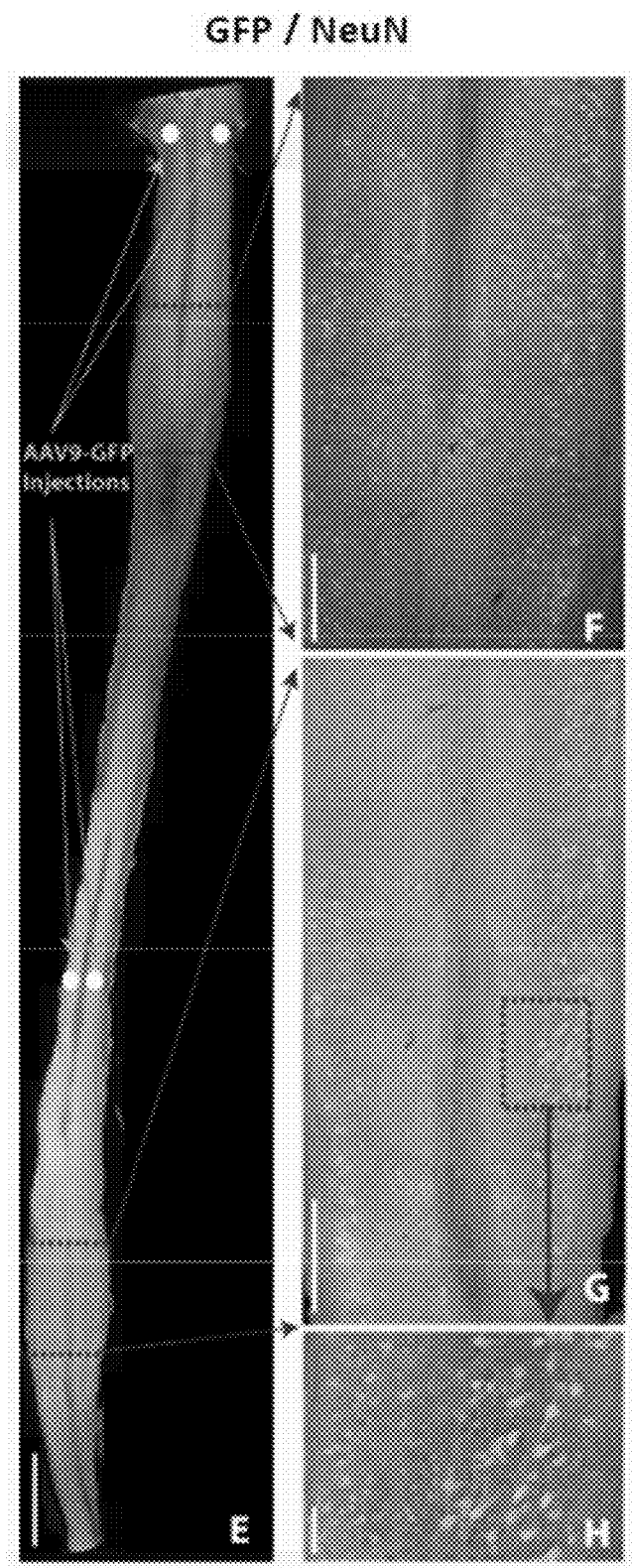

SPINAL SUBPIAL GENE DELIVERY SYSTEM

CROSS-REFERENCE TO RELATED APPLICATIONS

This application is a continuation-in-part of U.S. application Ser. No. 15/544,973, filed Jul. 20, 2017, which is a U.S. national phase application under 35 USC § 371 of international patent application no. PCT/US2015/065704, filed Dec. 15, 2015, which claims the benefit of priority from U.S. Provisional Application No. 62/110,340, filed on Jan. 30, 2015. This application also claims the benefit of priority from U.S. provisional application No. 62/413,267, filed Oct. 26, 2016. The entire content of each of application is incorporated herein by reference.

BACKGROUND OF THE INVENTION

Field of the Invention

The invention relates generally to gene therapy and more specifically to a method and system for delivery genes and oligonucleotides into the subpial space of a mammal to effect spinal trans-parenchymal infection thereof.

Background Information

Currently used approaches to deliver vectors or antisense oligonucleotides (ASOs) into spinal parenchyma involve two techniques, each having a substantial limitation as compared to the present invention.

First, intrathecal delivery is used when vectors or ASO is injected into spinal intrathecal space (i.e., outside of the pial membrane). Using this approach no deep parenchymal transgene expression is seen after AAV9 delivery. Only a subpopulation of A-motoneurons and primary afferents is infected due to the impermeability of the pial membrane to AAV9. While intrathecal delivery of ASO may lead to good penetration of ASO into spinal parenchyma, ASO is seen throughout the entire spinal cord (i.e., from cervical to sacral segments). As such, no segment-restricted distribution of ASO can be achieved by intrathecal delivery.

Second, a direct spinal parenchymal injection may be used. By using this approach a segment-specific transgene expression or ASO distribution can be achieved in spinal parenchyma. However, a major limitation of this technique is its invasive nature because direct spinal parenchymal needle penetration is required.

Thus, a need exists for a subpial delivery system that provides near complete spinal parenchymal AAV9-mediated gene expression or ASO distribution in both white and grey matter.

SUMMARY OF THE INVENTION

Effective in vivo use of AAV-based vectors to achieve gene-specific silencing or upregulation in the central nervous system has been limited by the inability to provide more than limited deep parenchymal expression in adult animals using delivery routes with the most clinical relevance (i.e., intravenous or intrathecal). Accordingly, the present invention demonstrates that the spinal pia membrane represents a primary barrier limiting effective AAV9 penetration into the spinal parenchyma after intrathecal AAV9 delivery. Thus, the present invention provides a method and system for delivery genes and oligonucleotides into spinal parenchyma of large animals and humans.

Accordingly, in one aspect, the invention provides a method of spinal trans-parenchymal infection of a nucleic acid molecule in a subject. The method includes administering a nucleic acid molecule to the subpial space of a subject. The subject may be a mammal, such as a human. In various embodiments, the step of administering includes exposing a spinal segment of a vertebra of the subject, creating a pial opening within the spinal segment, advancing a catheter through the pial opening and into subpial space, and delivering the nucleic acid molecule to the subpial space of the subject. The pial opening may be created by puncturing the pia with an L-shaped stainless steel tube and the catheter is advanced through the tube into the subpial space. In various embodiments, the nucleic acid molecule is administered in a mixture containing about 1-10% dextrose. In various embodiments, the nucleic acid molecule is a vector or an antisense oligonucleotide (ASO). The vector may be a lentiviral vector, adenoviral vector, or an adeno-associated vector, such as an AAV9 particle. In certain embodiments, the vector comprises a nucleic acid molecule encoding a protein or functional RNA that modulates or treats a neurodegenerative disorder, such as amyotrophic lateral sclerosis (ALS), Huntington's disease, Alzheimer's disease, Parkinson's disease.

In certain embodiments, the nucleic acid molecule is delivered as a single injection. In certain embodiments, the method further includes administering one or more second subpial injections of the nucleic acid molecule into a different spinal segment of the vertebra of the subject. In certain embodiments, the method further includes administering one or more intrathecal injections of the nucleic acid molecule to the subject.

In another aspect, the invention provides a gene delivery system. The system includes an L-shaped guide tube configured to puncture the pia of a subject, a catheter slidingly disposed within the guide tube and configured to be advanced into subpial space of a spinal segment of a vertebra of the subject, and a reservoir in fluid communication with the catheter and containing a composition comprising a nucleic acid molecule. In various embodiments, the L-shaped guide tube may be a 16-26G stainless steel tube, and the catheter may be formed from polyethylene tubing, such as PE-5 or PE-10.

In another aspect, the invention provides a method of delivering a nucleic acid molecule to the subpial space of a subject. The method includes exposing a spinal segment of a vertebra of the subject, creating a pial opening within the spinal segment, positioning above the spinal segment the gene delivery system described herein, advancing the catheter through the pial opening and into subpial space, and delivering the nucleic acid molecule to the subpial space of the subject. In various embodiments, the nucleic acid molecule is delivered in a mixture containing about 1-10% dextrose. The nucleic acid molecule is a vector or an antisense oligonucleotide (ASO). The vector is a lentiviral vector, adenoviral vector, or an adeno-associated vector, such as an AAV9 particle. The subject may be a mammal, such as a human being.

BRIEF DESCRIPTION OF THE DRAWINGS

FIGS. 1A-1J are pictorial diagrams showing subpial AAV9 delivery and macroscopically defined spinal cord surface transgene expression. FIG. 1A shows a schematic diagram of a spinal cord, meninges and a subpially placed PE-10 catheter in pig. FIG. 1B shows a catheter guiding tube (18G) with a sharp pia-penetrating tip (insert), which is used to penetrate the pia and to advance the PE-10 catheter into the subpial space. FIGS. 1C-1E are pictorial diagrams showing the progression of placement of the catheter into the subpial space: the dura mater is first cut open (FIG. 1C) and the catheter is advanced into the subpial space (FIGS. 1D and 1E). An air bubble that was injected into the subpial space can be seen (FIG. 1D-asterisk). FIGS. 1F and 1G show surface GFP fluorescence densitometry showing an intense signal in both pig and rat spinal cords with the most intense GFP fluorescence seen at the epicenter of lumbar subpial injection. The presence of intense RFP fluorescence in the spinal cord parenchyma detected macroscopically in pig thoracic spinal cord (FIGS. 1H and 1J). A clear high level of RFP expression in ventral roots can also be seen (FIG. 1H-insert). No fluorescence in the control non-injected spinal cord can be identified (FIG. 1I).

FIGS. 3A-3G are pictorial diagrams showing effective parenchymal AAV9-mediated transgene expression after a single bolus subpial AAV9-UBI-RFP injection in an adult pig. FIGS. 3A and 3B show horizontal spinal cord sections taken from mid-thoracic spinal cord of a pig injected with AAV9-UBI-RGF six weeks previously. Intense RFP expression can be seen throughout the whole region including the white and gray matter. Staining with NeuN antibody (green) shows that virtually all neurons are also RFP positive. FIGS. 3C-3G show images of a transverse spinal cord section taken from the subpially-injected region showing transversally-cut RFP+ axons in the dorsal (DF) lateral (LF) and ventral (VF) funiculus (box inserts). RFP expression can also be seen in GFAP-stained astrocytes (insert; RFP/GFAP). High density RFP+ terminal boutons surrounding RFP-expressing α-motoneuron (FIGS. 3D and 3E) and interneurons (FIGS. 3F and 3G) can be seen. (Scale bars: FIGS. 3A-3C=500 µm; FIGS. 3D, 3F=30 µm).

FIGS. 4A-4C are pictorial diagrams showing potent GFP expression in descending motor axons in lumbar spinal cord after mid-thoracic subpial AAV9 injection in a pig. FIGS. 4A and 4B show a transverse spinal cord section taken from the lumbar spinal cord after subpial AAV9-UBI-GFP injection into the mid-thoracic subpial space six weeks previously. Intense GFP expression in transversal cut axons in lateral (LF) and ventral (VF) funiculus can be seen (white asterisks). A relatively lower density of GFP+ axons in the dorsal funiculus was identified (DF). Correspondingly, a high density of GFP+ motor axons projecting into the gray matter localized between the dorsal horn (DH) and ventral horn (VH) can also be seen. FIG. 4C shows a higher resolution confocal image showing very fine arborization of GFP+ axons and terminal boutons in the central gray matter. (Scale bars: FIG. 4A=1000 µm; FIG. 4C=30 µm), (DH-dorsal horn, VH-ventral horn, DF-dorsal funiculus, LF-lateral funiculus, VF-ventral funiculus).

FIGS. 5A-5E show retrogradely-labeled pyramidal neurons in the motor cortex of a pig at six weeks after a mid-thoracic, single AAV9-UBI-GFP injection. FIGS. 5F-5J show a comparable level of GFP expression in neurons localized in the brain stem. FIG. 5K shows the presence of large retrogradely-labeled motor GFP+ axons in the medulla oblongata (medullary pyramids). FIG. 5L shows a high density of anterogradely-labeled sensory afferents in formatio reticularis. (Scale bars: FIGS. 5A-5E and 5G-5J=50 µm; FIGS. 5K and 5L=50 µm).

FIGS. 6A-6D show bilateral retrogradely-GFP-labeled pyramidal neurons in the motor cortex of rat at eight weeks after upper-cervical single AAV9-UBI-GFP injection. FIGS. 6E-6G show bilateral neuronal GFP expression in the nucleus ruber. (Scale bars: FIGS. 6A, 6B, 6E, and 6F=50 µm; FIGS. 6C and 6D=50 µm; FIG. 6G=20 µm).

FIGS. 7A-7G are pictorial diagrams showing differential regional spinal transgene expression after intrathecal AAV9-UBI-GFP vs. subpial AAV9-UBI-RFP delivery in a rat. FIG. 7A shows that lumbar intrathecal injection of AAV9-UBI-GFP led to the preferential GFP expression in the dorsal funiculus (DF), dorsal root (DR) and ventral root entry zone (white box insert No. 2). Subpial AAV9-UBI-RFP injection into the upper cervical spinal cord led to clear descending motor tracts labeling. FIG. 7B shows expression of GFP in dorsal root ganglion cells (L4) after lumbar intrathecal AAV9-UBI-GFP injection. FIGS. 7C and 7D show that intense GFP expression after intrathecal AAV9-UBI-GFP injection is seen in the dorsal root (DR) and in primary afferents boutons in the deeper dorsal horn (white asterisk), but no expression in dorsal horn NeuN+ neurons can be identified. FIG. 7E shows that no co-localization of GFP and RFP in dorsal funiculus (DF) can be seen (white insert from FIG. 7A, No. 1). FIG. 7F shows GFP expression in glial cells localized in the ventral root entry zone resulting from intrathecal AAV9-UBI-GFP injection (white insert from FIG. 7A, No. 2). FIG. 7G shows that some retrogradely-labeled GFP expressing α-motoneurons surrounded by GFP+ primary Ia afferents can be seen in animals injected with AAV9-UBI-GFP. (Scale bars: FIG. 7A=500 µm; FIGS. 7B-7G=30 µm), (DR-dorsal root, DH-dorsal horn, VH-ventral horn, DF-dorsal funiculus).

FIGS. 9A-9D show widespread GFP expression in neurons and white matter tracts in lower thoracic and upper lumbar spinal cord after L1 subpial AAV9-UBI-GFP injection. Virtually all neurons in the horizontally cut section (FIG. 9A) show GFP expression. In transversally cut sections GFP+ neurons can be seen throughout the whole gray matter between laminae I-IX (FIGS. 9B-9D). Numerous NeuN-stained neurons expressing GFP in the superficial dorsal horn (Laminae I-III) and in the ventral horn can be seen. FIGS. 9E and 9F show a high density of GFP+ descending motor fibers in the lumbar spinal cord after upper cervical AAV9-UBI-GFP injection. FIG. 9E shows a high density confocal image depicting easily recognizable GFP+ terminal boutons in the gray matter. (Scale bars: FIG. 9A=1000 μm; FIGS. 9B-9D=30 μm; FIG. 9E=50 μm; FIG. 9F=100 μm), (WM-white matter, GM-gray matter, DH-dorsal horn, VH-ventral horn, DF-dorsal funiculus).

FIG. 13A shows the two bilateral injections of AAV9-UBI-GFP (1.5 or 3 μL injections each) were delivered into the upper lumbar subpial space, and animals were perfusion-fixed 14 days after AAV9 delivery. FIG. 13B shows intense GFP expression in the gray (inside the dotted area) and white matter, extending from the lumbar to the upper thoracic segments, can be seen in animals injected with 3+3 μL of AAV9 (left and middle columns). FIGS. 13C, 13D, 13E, and 13F show co-staining of transverse spinal cord sections taken from the lumbar enlargement in animals injected with 3+3 μL of AAV9 show GFP expression in virtually all ChAT (α-motoneuron marker)-positive α-motoneurons (FIGS. 13C and 13F) and NeuN-positive interneurons in the dorsal horn (FIG. 13D) and intermediate zone (FIG. 13E). Scale bars=1,000 μm (B); 30 μm (FIG. 13C); 100 μm (FIGS. 13D-13F). DH: dorsal horn; LV: lamina V; VH: ventral horn.

FIGS. 14A-14H are pictorial diagrams showing a comparison of spinal GFP expression after spinal subpial cervical versus spinal subpial cervical plus subpial lumbar AAV9-UBI-GFP delivery in adult mice. FIGS. 14A, 14B, 14C and 14D show horizontal section cuts through the whole length of the spinal cord in an animal that previously received upper cervical subpial injections of AAV9-UBI-GFP (5+5 μL). Intense GFP expression in the white and gray matter in the cervical region can be seen (FIG. 14B). In the lumbar spinal cord, a high density of GFP+ descending axons in the lateral funiculus (LF) and the gray matter between NeuN-positive but GFP-negative neurons can be identified (FIGS. 14C and 14D). FIGS. 14E, 14F, 14G, and 14H show horizontal section cuts through the whole length of the spinal cord in an animal previously receiving upper cervical and upper lumbar subpial injections of AAV9-UBI-GFP (5+5 μL at the cervical and lumbar level). Intense GFP fluorescence throughout the whole spinal cord (white and gray matter) can be seen. Individual NeuN-stained interneurons and α-motoneurons co-expressing GFP can readily be identified in cervical (FIG. 14F) and lumbar (FIGS. 14G and 14H) spinal gray matter. Scale bars=2,000 μm (FIGS. 14A and 14E); 500 μm (FIGS. 14B, 14C, 14F, and 14G); 100 μm (FIGS. 14D and 14H). C: cervical; L: lumbar; WM: white matter; GM: gray matter; LF: lateral funiculus.

FIG. 15A shows a low-power image depicting the presence of intense GFP positivity in the cervical spinal cord, medulla oblongata, cerebellum, and motor cortex (MC). FIG. 15B shows a higher-power image taken from a sagittal brain section and showing the presence of GFP fluorescence in neurons in the reticular formation (RF), nucleus ruber (NR), and axons of the spino-cerebellar tract (SCT). FIG. 15C shows a lower-power image taken from coronal brain sections showing the presence of GFP fluorescence in pyramidal neurons in the motor cortex (MC) and in the terminals of the spinothalamic tract in areas of the reticular thalamic nuclei (STT). FIG. 15D shows a high-power image demonstrating an intense GFP expression in pyramidal neurons in the motor cortex. Scale bars=2,000 μm (FIG. 15A); 1,000 μm (FIGS. 15B and 15C); 60 μm (FIG. 15D).

DETAILED DESCRIPTION OF THE INVENTION

The present invention provides a method and system for delivery genes and oligonucleotides into spinal parenchyma of large animals and humans.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Figure 1A:
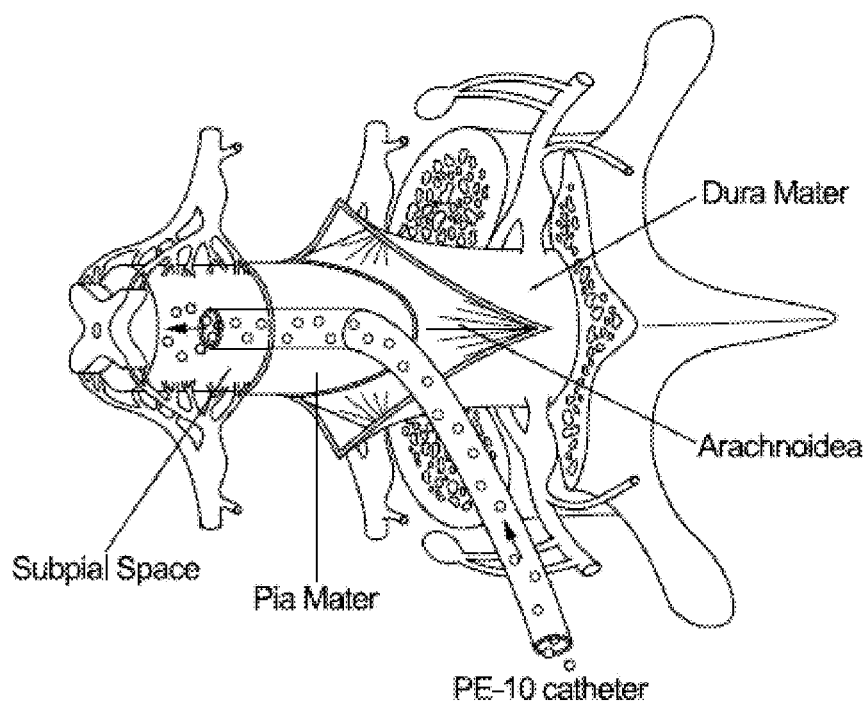

As used herein, the term "pia mater" refers to the innermost layer of the meninges, the membranes surrounding the brain and spinal cord (FIG. 1A). Pia mater is a thin fibrous tissue that is impermeable to fluid. This allows the pia mater to enclose cerebrospinal fluid. By containing this fluid the pia mater works with the other meningeal layers to protect and cushion the brain. Spinal pia mater encloses the surface of the medulla spinalis, or spinal cord, and is attached to it through a connection to the anterior fissure. Accordingly, the term "subpial" refers to being situated or occurring beneath the pia mater.

As used herein, the term "parenchyma" refers to the functional tissue of an organ as distinguished from the connective and supporting tissue. Thus, the term "spinal parenchayma" refers to the various known anatomical tissues of the spinal cord, including, but not limited to the grey matter, white matter, the dura mater, arachnoid mater, pia mater, posterior and anterior funiculi, posterior and anterior spinocerebellar tracts, etc.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, "treatment" refers to a clinical intervention made in response to a disease, disorder or physiological condition manifested by a patient/subject or to which a patient/subject may be susceptible. The aim of treatment includes, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

As used herein, a "pluripotent cell" refers to a cell derived from an embryo produced by activation of a cell containing DNA of all female or male origin that can be maintained in vitro for prolonged, theoretically indefinite period of time in an undifferentiated state that can give rise to different differentiated tissue types, i.e., ectoderm, mesoderm, and endoderm. "Embryonic stem cells" (ES cells) are pluripotent stem cells derived from the inner cell mass of a blastocyst, an early-stage preimplantation embryo.

The ability of hematopoietic stem and progenitor cells (HSPCs) to self-renew and differentiate is fundamental for the formation and maintenance of life-long hematopoiesis and deregulation of these processes may lead to severe clinical consequences. HSPCs are also highly valuable for their ability to reconstitute the hematopoietic system when transplanted and this has enabled their use in the clinic to treat a variety of disorders including bone marrow failure, myeloproliferative disorders and other acquired or genetic disorders that affect blood cells.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, a "regulatory gene" or "regulatory sequence" is a nucleic acid sequence that encodes products (e.g., transcription factors) that control the expression of other genes.

As used herein, a "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from eukaryotic mRNA, genomic DNA sequences from eukaryotic DNA, and synthetic nucleic acids. A transcription termination sequence will usually be located 3' to the coding sequence.

As used herein, a "promoter" is defined as a regulatory DNA sequence generally located upstream of a gene that mediates the initiation of transcription by directing RNA polymerase to bind to DNA and initiating RNA synthesis. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular compound or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process.

As used herein, the terms "functionally linked" and "operably linked" are used interchangeably and refer to a functional relationship between two or more DNA segments, in particular gene sequences to be expressed and those sequences controlling their expression. For example, a promoter/enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')2 fragments, disulfide-linked Fvs (sdFv) fragments, for example, as produced by a Fab expression library, anti-idiotypic (anti-Id) antibodies, intrabodies, nanobodies, synthetic antibodies, and epitope-binding fragments of any of the above.

As used herein, a "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors (AV), adeno-associated virus vectors (AAV), herpes virus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference). In one aspect of the invention, a lentivirus or an adenovirus vector is utilized. Adenoviruses are double-stranded DNA viruses, where both strands of DNA encode genes. The genome encodes about thirty proteins. In another aspect of the invention, an adeno-associated virus vector is utilized.

The term "adenovirus" refers to over 40 adenoviral subtypes isolated from humans, and as many from other mammals and birds. See, Strauss, "Adenovirus infections in humans," in *The Adenoviruses*, Ginsberg, ed., Plenum Press, New York, N.Y., pp. 451-596 (1984). Recombinant adenovirus vectors, such as those based on the human adenovirus 5 (as described by McGrory W J, et al., Virology 163: 614-617, 1988) are missing essential early genes from the adenovirus genome (usually E1A/E1B), and are therefore unable to replicate unless grown in permissive cell lines that provide the missing gene products in trans. In place of the missing adenovirus genomic sequences, a transgene of interest can be cloned and expressed in tissue/cells infected with the replication-defective adenovirus. Although adenovirus-based gene transfer does not generally result in stable integration of the transgene into the host genome (less than 0.1% adenovirus-mediated transfections result in transgene incorporation into host DNA), adenovirus vectors can be propagated in high titer and transfect non-replicating cells; and, although the transgene is not passed to daughter cells, this is suitable for gene transfer to adult cardiac myocytes, which do not actively divide. Retrovirus vectors provide stable gene transfer, and high titers are now obtainable via retrovirus pseudotyping (Burns, et al., *Proc. Natl. Acad. Sci.* (USA) 90: 8033-8037, 1993), but current retrovirus vectors are generally unable to efficiently transduce nonreplicating cells Additional references describing adenovirus vectors and other viral vectors which could be used in the methods of the present invention include the following: Horwitz, M. S., Adenoviridae and Their Replication, in Fields, B., et al. (eds.) *Virology*, Vol. 2, Raven Press New York, pp. 1679-1721, 1990); Graham, F., et al., pp. 109-128 in *Methods in Molecular Biology*, Vol. 7: Gene Transfer and Expression Protocols, Murray, E. (ed.), Humana Press, Clifton, N.J. (1991); Miller, N., et al., FASEB Journal 9: 190-199, 1995; Schreier, H, *Pharmaceutica Acta Helvetiae* 68: 145-159, 1994; Schneider and French, Circulation 88:1937-1942, 1993; Curiel D. T., et al., *Human Gene Therapy* 3: 147-154, 1992; Graham, F. L., et al., WO 95/00655 (5 Jan. 1995); Falck-Pedersen, E. S., WO 95/16772 (22 Jun. 1995); Denefle, P. et al., WO 95/23867 (8 Sep. 1995); Haddada, H. et al., WO 94/26914 (24 Nov. 1994); Perricaudet, M. et al., WO 95/02697 (26 Jan. 1995); Zhang, W., et al., WO 95/25071 (12 Oct. 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996).

An adeno-associated virus (AAV) is a small (26 nm) replication-defective, nonenveloped virus that depends on the presence of a second virus, such as adenovirus or herpes virus, for its growth in cells. AAV is not known to cause disease and induces a very mild immune response. AAV can infect both dividing and non-dividing cells and may incorporate its genome into that of the host cell. Aspects of the invention provide methods for delivering a transgene to the spinal tissue in a subject using recombinant AAV-based gene transfer.

Additional references describing AAV vectors which could be used in the methods of the present invention include the following: Carter, B., Handbook of Parvoviruses, vol. I, pp. 169-228, 1990; Berns, *Virology*, pp. 1743-1764 (Raven Press 1990); Carter, B., *Curr. Opin. Biotechnol.*, 3: 533-539, 1992; Muzyczka, N., *Current Topics in Microbiology and Immunology*, 158: 92-129, 1992; Flotte, T. R., et al., *Am. J. Respir. Cell Mol. Biol.* 7:349-356, 1992; Chatterjee et al., *Ann. NY Acad. Sci.*, 770: 79-90, 1995; Flotte, T. R., et al., WO 95/13365 (18 May 1995); Trempe, J. P., et al., WO 95/13392 (18 May 1995); Kotin, R., *Human Gene Therapy*, 5: 793-801, 1994; Flotte, T. R., et al., *Gene Therapy* 2:357-362, 1995; Allen, J. M., WO 96/17947 (13 Jun. 1996); and Du et al., *Gene Therapy* 3: 254-261, 1996. See also, U.S. Pat. No. 8,865,881, incorporated herein by reference.

An "effective amount" of an AAV is an amount sufficient to infect a sufficient number of cells of a target tissue in a subject. An effective amount of an AAV may be an amount sufficient to have a therapeutic benefit in a subject, e.g., to extend the lifespan of a subject, to improve in the subject one or more symptoms of disease, e.g., a symptom of a neurodegenerative disease. The effective amount may depend on a variety of factors such as, for example, the species, age, weight, health of the subject, and the tissue to be targeted, and may thus vary among subject and tissue. An effective amount may also depend on the mode of administration. For example, targeting a CNS tissue by intravascular injection may require different (e.g., higher) doses, in some cases, than targeting CNS tissue by intrathecal or intracerebral injection. However, the potent transgene expression seen throughout the spinal cord and in the supraspinal brain centers appears to demonstrate the clear advantage of the claimed methods over intrathecal AAV delivery, which is characterized by selective transgene expression in a subpopulation of α-motoneurons and primary afferents (but is not present in neurons in the deeper spinal cord laminae).

In some cases, multiple doses of an AAV are administered. An effective amount may also depend on the particular AAV used. For example, dosages for targeting a CNS tissue may depend on the serotype (e.g., the capsid protein) of the AAV. For example, the AAV may have a capsid protein of an AAV serotype selected from the group consisting of: AAV1, AAV2, AAV5, AAV6, AAV6.2, AAV7, AAV8, AAV9, rh.10, rh.39, rh.43 and CSp3. In certain embodiments, the effective amount of AAV is $10^{10}$, $10^{11}$, $10^{12}$, $10^{13}$, or $10^{14}$ genome copies per kg. In certain embodiments, the effective amount of AAV is $10^{10}$, $10^{11}$, $10^{12}$, $10^{13}$, $10^{14}$, or $10^{15}$ genome copies per subject.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516-544, 1987). For example, when cloning in bacterial systems, inducible promoters such as pL of bacteriophage, plac, ptrp, ptac (ptrp-lac hybrid promoter) and the like can be used. When cloning in mammalian cell systems, promoters derived from the genome of mammalian cells, for example, a human or mouse metallothionein promoter, or from mammalian viruses, for example, a retrovirus long terminal repeat, an adenovirus late promoter or a vaccinia virus 7.5K promoter, can be used. Promoters produced by recombinant DNA or synthetic techniques can also be used to provide for transcription of the inserted GDF receptors coding sequence.

As used herein a "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein (GFP), enhanced green fluorescent protein, red fluorescent protein (RFP), luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

As used herein, the terms "transformed" or "transfected" are used interchangeably and refer to the process by which exogenous DNA or RNA is transferred or introduced into an appropriate host cell. Additionally, nucleic acids encoding other heterologous proteins may be introduced into the host cell. Such transfected cells include stably transfected cells wherein the inserted DNA is rendered capable of replication in the host cell. Typically, stable transfection requires that the exogenous DNA be transferred along with a selectable marker nucleic acid sequence, such as for example, a nucleic acid sequence that confers antibiotic resistance, which enables the selection of the stable transfectants. This marker nucleic acid sequence may be ligated to the exogenous DNA or be provided independently by simultaneous cotransfection along with the exogenous DNA. Transfected cells also include transiently expressing cells that are capable of expressing the RNA or DNA for limited periods of time. The transfection procedure depends on the host cell being transfected. It can include packaging the polynucleotide in a virus as well as direct uptake of the polynucleotide. Transformation can result in incorporation of the inserted DNA into the genome of the host cell or the maintenance of the inserted DNA within the host cell in plasmid form. Methods of transformation/transfection are well known in the art and include, but are not limited to, direct injection, such as microinjection, viral infection, particularly replication-deficient adenovirus infection, electroporation, lipofection, and calcium phosphate-mediated direct uptake.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA).

For nucleic acids encoding proteins, a polyadenylation sequence may be inserted following the transgene sequences and before the 3' AAV ITR sequence. An AAV construct useful in the present invention may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. For example, an IRES sequence would be used to produce a protein that contain more than one polypeptide chains. Selection of these and other common vector elements are conventional and many such sequences are available. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). Other appropriate tissue specific promoters will be apparent to the skilled artisan. In some embodiments, the promoter is a chicken Beta-actin promoter.

In some aspects, the invention provides an AAV vector for use in methods of preventing or treating one or more gene defects (e.g., heritable gene defects, somatic gene alterations) in a mammal, such as for example, a gene defect that results in a polypeptide deficiency or polypeptide excess in a subject, and particularly for treating or reducing the severity or extent of deficiency in a subject manifesting a CNS-associated disorder linked to a deficiency in such polypeptides in cells and tissues. In some embodiments, the methods involve administration of an AAV vector that encodes one or more therapeutic peptides, polypeptides, shRNAs, microRNAs, antisense nucleotides, etc., in a pharmaceutically-acceptable carrier to the subject in an amount and for a period of time sufficient to treat the CNS-associated disorder in the subject having or suspected of having such a disorder. "Antisense inhibition" refers to the production of antisense RNA transcripts capable of suppressing the expression of protein from an endogenous gene or a transgene.

Thus, the AAV vector may comprise as a transgene, a nucleic acid encoding a protein or functional RNA that modulates or treats a CNS-associated disorder. The following is a non-limiting list of genes associated with CNS-associated disorders: neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxlase (TH), GTP-cyclohydrolase (GTPCH), aspartoacylase (ASPA), superoxide dismutase (SOD1) and amino acid decorboxylase (AADC). For example, a useful transgene in the treatment of Parkinson's disease encodes TH, which is a rate limiting enzyme in the synthesis of dopamine. A transgene encoding GTPCH, which generates the TH cofactor tetrahydrobiopterin, may also be used in the treatment of Parkinson's disease. A transgene encoding GDNF or BDNF, or AADC, which facilitates conversion of L-Dopa to DA, may also be used for the treatment of Parkinson's disease. For the treatment of ALS, a useful transgene may encode: GDNF, BDNF or CNTF. Also for the treatment of ALS, a useful transgene may encode a functional RNA, e.g., shRNA, miRNA, that inhibits the expression of SOD1. For the treatment of ischemia a useful transgene may encode NAIP or NGF. A transgene encoding Beta-glucuronidase (GUS) may be useful for the treatment of certain lysosomal storage diseases (e.g., Mucopolysacharidosis type VII (MPS VII)). A transgene encoding a prodrug activation gene, e.g., HSV-Thymidine kinase which converts ganciclovir to a toxic nucleotide which disrupts DNA synthesis and leads to cell death, may be useful for treating certain cancers, e.g., when administered in combination with the prodrug. A transgene encoding an endogenous opioid, such a β-endorphin may be useful for treating pain. Other examples of transgenes that may be used in the AAV vectors of the invention will be apparent to the skilled artisan (See, e.g., Costantini L C, et al., Gene Therapy (2000) 7, 93-109).

Over the past decade several experimental and/or clinical studies reported on the successful use of AAV-based vectors (particularly AAV9) for CNS-targeted gene delivery. These studies established unequivocally the value of AAV-based-delivery vectors as a tool to achieve a potent gene upregulation or silencing in targeted CNS regions and have provided evidence that this therapeutic approach can effectively be used in treatment of numerous neurodegenerative disorders including ALS, SMA, muscle spasticity and chronic pain. Despite these encouraging data and extensive preclinical animal studies, a detailed mechanism on how the AAV vectors penetrate in brain or spinal cord parenchyma after using different routes of AAVs delivery (systemic, intrathecal) have not been fully understood. These data are critical for development of new and more effective AAV delivery protocols which would be equally potent in young and in fully developed adult animal and human subjects. In general, the preclinical animal studies can be categorized into several groups based on the developmental stage of when the animal is employed or the route the AAV is delivered (e.g., systemic or intrathecal). Depending on the parameters used in the individual studies, the level of transgene expression and the specific cell populations (neuronal and/or glial) that are being infected varies greatly.

The early studies demonstrated that the systemic-vein (iv) injection of AAV9-GFP in neonatal mice leads to widespread CNS GFP expression, including dorsal root ganglia, spinal motoneurons (MN) and neurons in brain (neocortex, hippocampus, cerebellum). Using adult mice, iv-delivered AAV9-GFP leads to a preferential astrocyte infection throughout the entire CNS, but only limited neuronal expression is seen (Foust, et al. (2009). Intravascular AAV9 preferentially targets neonatal neurons and adult astrocytes. *Nature biotechnology* 27: 59-65). Comparable data were reported demonstrating widespread spinal MN GFP expression after systemic (iv) delivery of AAV9 in neonatal mice (Duque, et al. (2009). Intravenous administration of self-complementary AAV9 enables transgene delivery to adult motor neurons. *Molecular therapy: the journal of the American Society of Gene Therapy* 17: 1187-1196). In addition, the same group demonstrated successful transgene expression in spinal MN once AAV9 was delivered iv in adult mice or cats. Similar to these two studies, Gray, et al. have shown CNS neuronal GFP expression after iv AAV9 administration in adult mice, however, only limited transduction efficiency was seen in juvenile non-human primates; compared previous studies, where a clear shift from neuronal to glial expression was seen in the brain (Gray, et al. (2011). Preclinical differences of intravascular AAV9 delivery to neurons and glia: a comparative study of adult mice and nonhuman primates. *Molecular therapy: the journal of the American Society of Gene Therapy* 19: 1058-1069).

Given the apparent limited neuronal expression after systemic iv AAV9 delivery in adult animals, the use of intrathecal route (to bypass the blood brain barrier) was explored in several studies. Using one-year-old, 2 kg BW, non-human primates (Cynomolgus macaques), it was demonstrated that a single lumbar-intrathecal injection of AAV9-CB-GFP led to 50-75% MN transduction in the entire spinal cord at two weeks after AAV9 injection. Similarly, in another study using juvenile 2- to 3-year-old non-human primates (Cynomolgus macaques) or young (2-month-old) pigs, potent MN transduction was seen throughout the entire spinal cord after intra-cisternal or combined cisternal-lumbar intrathecal AAV9 delivery. In addition, in the same study GFP expression was observed in dorsal root ganglion cells, motor cortex and in Purkinje cells in the cerebellar cortex. In a more recent study, comparable lumbar MN GFP expression was seen in non-human primates (Cynomolgus macaques) after intra-cisternal AAV9-GFP injection.

Interestingly, in all studies that employ a cisternal or lumbo-sacral intrathecal delivery route, the available histological data showed a very specific spinal transgene expression pattern. It is characterized by intense expression in α-motoneurons, however, the ventral horn interneurons that are residing in close proximity to the GFP-expressing α-motoneurons appear to be transgene negative. Similarly, potent transgene expression is seen in dorsal root ganglion cells and primary afferents. However, small interneurons localized in the superficial dorsal horn or in the intermediate zone show no transgene expression.

This high level of transgene expression selectivity and lack of infection in deeper gray matter cells indicate the presence of a well-developed regulatory-barrier system (in addition to the blood-brain barrier), which prevents the penetration of virus into deeper spinal compartments from the intrathecal space. Based on a well described anatomical organization of spinal meninges, it had been hypothesized that the pia mater represents a key barrier that regulates the penetration of AAV into the spinal parenchyma after intrathecal AAV delivery. It was therefore speculated that the high level of transgene expression seen in MN and DRGs cells reported after intrathecal delivery is likely mediated by the preferential retro- and anterograde infection of axons projecting into and out of the spinal parenchyma and transpassing the intrathecal space (i.e., ventral and dorsal roots).

Accordingly, to address this issue, the present invention provides a subpial vector delivery method in mammals, and demonstrates that this delivery route leads to potent transspinal transgene expression infecting the entire population of neurons in the gray matter of subpially injected segments. In addition, near complete infection of descending and ascending axons was achieved, and corresponded with the transgene expression in brain centers (i.e., motor cortex, nucleus ruber).

Thus, the method and delivery system provided herein permit spinal subpial gene therapy, such as AAV9 vector, stem cell or antisense oligonucleotide (ASO) delivery, into spinal parenchyma in large animals or in humans. To deliver AAV9 or ASO into the subpial space a new delivery system was designed to include a guiding tube bended at 90° and catheter (e.g., PE-5 or PE-10), which permits precise guidance and placement of the subpial catheter into the dorsal subpial space of targeted spinal cord segments. After placement of the catheter, the AAV9 or ASO is infused for a certain amount of time before being removed. In various embodiments, the AAV9 or ASO is infused for approximately 2-3 minutes.

As used herein, the term "PE-10" refers to polyethylene tubing having an inner diameter of approximately 0.010 inches. In certain embodiments, the inner diameter of the PE-10 tubing will be about 0.011 inches. Likewise, the term "PE-5" refers to polyethylene tubing having an inner diameter of approximately 0.005 inches. In certain embodiments, the inner diameter of the PE-5 tubing will be about 0.008 inches.

Accordingly, the claimed system and method provides subpial delivery (i.e., bypassing the pial membrane), which provides near complete spinal parenchymal AAV9-mediated gene expression or distribution in both white and grey matter of the subject being treated. Currently available non-invasive techniques do not permit a comparable level of spinal parenchymal transgene expression or well controlled segment-specific gene silencing.

For example, by using shRNA-silencing vectors, it is expected that a highly effective decrease in the expression of mutated genes (e.g., SOD in the case of the inherited form of ALS) will be achieved throughout the spinal cord as well as in spinally-projecting brain motor nuclei. Thus, because of the highly effective infection of the spinal white matter axons, therapeutic genes (e.g., encoding growth factors) can be upregulated to promote axonal sprouting in spinal trauma-injured animals. As shown herein, by manipulating the volume or the titer of subpially-delivered virus as well as the site of subpial injection, the expression of the transgene can be targeted to a discrete region of the spinal cord (e.g., the unilateral dorsal horn). Localized transgene expression can potentially be used in pain or muscle spasticity-modifying treatment by upregulating inhibitory neurotransmitter systems (e.g., GABA) or inhibiting excitatory systems (e.g., the glutamate-coupled receptor system). Further, in addition to AAV delivery, other molecules or vectors with poor blood-brain barrier permeability (e.g., micro RNA) will likely be more effectively delivered into the spinal parenchyma after subpial delivery. These can effectively be tested by using the technique described herein. Finally, as demonstrated in the current study, the subpial technique can successfully be used in adult mice with average bodyweights (BW) between 20 and 30 g. Thus, it is likely that the same technique and experimental setup can be employed in other animal species with similar BW (e.g., Sprague-Dawley (SD) rat pups). The BW of P6 and P21 SD rats is around 17 and 62 g, respectively. Using the rat pups during the early stage of postnatal development can be a useful tool to study the role of specific gene up- or downregulation in the development of spinal neural circuits and sensory and motor processing.

To place the subpial catheter in a mammalian subject, several sequential procedural steps may be followed to minimize potential spinal injury associated with instruments/catheter manipulation in the vicinity of the exposed "dura-free" spinal cord. In various embodiments, the use of caudal and cranial spinal clamps (placed just above and below the laminectomy) minimized spinal cord pulsation during catheter placement. Also in various embodiments, an "L" shaped catheter stainless steel guiding tube (e.g., a 16-26 G stainless steel tube bended at) 90° mounted on an XYZ manipulator (as described in, for example, US Pub. No. 2015/0224331, incorporated herein by reference) is used for subpial catheter placement.

In certain embodiments, the pia is first punctured using a bent 30G needle. Once the tip of the penetrating 30G needle is in the subpial space for about 1-1.5 mm, the pia may be slightly lifted by 1-2 mm. The subpial catheter is then placed into the subpial space by advancing the catheter from the guiding tube. After the catheter is advanced into the targeted length, the penetrating needle tip of the guiding tube is removed from the subpial space. Once the vector injection is completed (typically over 2-5 min, and in some embodiments, over about 3 min), the catheter is pulled out of the subpial space and the dura is closed. By using this technical approach, placement of the subpial catheter may be accomplished within about 3-5 min from the moment of dura opening.

The subpial catheter described herein has been successfully placed in 17 pigs using this technique, achieving consistent and injury-free subpial catheter placement. In adult rats an identical technique is used, however, a PE-5 catheter is used instead. The data obtained using these adult rats and pigs demonstrates i) potent spinal parenchymal transgene expression in white and gray matter including neurons and glial cells after single bolus subpial AAV9 delivery, ii) delivery to almost all descending motor axon throughout the length of the spinal cord after cervical or thoracic subpial AAV9 injection, iii) potent retrograde transgene expression in brain motor centers (motor cortex and brain stem), and iv) safety of this approach by defining normal neurological function for up to three months after AAV9 delivery. Thus, subpial delivery of AAV-9 enables gene-based therapies with a wide range of experimental and clinical utilizations in adult mammals.

In one embodiment, a 16-26 G stainless steel tube bended at 90° is used as a guiding cannula for a PE-10 catheter. The guiding tube is positioned just above the spinal pia and the PE-catheter is then advanced into subpial space through a small pial opening (FIGS. 1A-1E). AAV9 is then infused into subpial space. In certain embodiments, the AAV9 is delivered in a mixture containing between 1-10% of dextran (10,000-30,000 MW) to permit a longer lasting deposition of AAV9 particles in spinal parenchyma. After AAV9-GFP delivery a consistent GFP expression may be seen throughout the spinal parenchyma at the level of injection and in axons projecting distally (into lumbar spinal cord) from AAV9 injected segments.

As demonstrated herein, a single subpial AAV9 injection led to potent parenchymal transgene expression spreading rostro-caudally for multiple segments. Thus, subpial AAV9 delivery leads to a wide-spread transgene expression in neurons throughout the gray matter and ascending and descending axons in subpial-injected segments. For example, in an adult pig spinal cord, the transgene spread was consistently seen in distances of about 10-15 cm from the point of administration. Expression was identified in neurons and glial cells in all gray matter laminae and in axons in ventral, lateral and dorsal funiculi confirming a near complete penetration of subpial-injected AAV9 vector throughout the spinal parenchyma. By analyzing transverse lumbar spinal cord sections in pigs which received a mid-thoracic AAV9-UBI-GFP injection (i.e., about 30 cm distance from the site of AAV9 delivery), virtually all descending motor axons appeared to be labeled at six weeks after AAV9 injection. Higher resolution confocal microscopy revealed a dense network of fine axonal arborizations with terminal boutons throughout the gray matter. Consistent with the level and distribution of infected axons in the white matter, retrogradely infected GFP-expressing neurons in the motor cortex and in the brain stem were identified. Similarly, centrally projecting sensory axons were identified in the reticular formation and in the thalamus.

By comparing the transgene expression pattern after subpial vs. intrathecal AAV9 delivery in rats, the present invention demonstrates a substantially different regional-cellular expression. As such, the pia mater represents a primary barrier for effective parenchymal penetration of AAV9 after intrathecal delivery.

First, after intrathecal delivery, the expression was only seen in regions and neuronal-glial pools which are morphologically associated with dorsal and ventral root entry zone. Thus, potent transgene expression was seen in primary afferents and was clearly present in the dorsal funiculi, primary afferents in the dorsal horn and Ia afferents projecting to the ventral horn. This transgene expression in primary afferents corresponded with a potent expression in dorsal root ganglion cells. Similarly, a clear expression was seen around the ventral root entry zone with some retrogradely-labeled α-motoneurons in the ventral horn. In contrast, however, the transgene expression was virtually absent in all other neurons between laminae I-VII and X, and no descending motor axons were labeled in the lateral or ventral funiculi. Similarly, the axons of the corticospinal tract in rats (localized on the base of dorsal funiculi), which were surrounded by GFP-expressing primary afferents, showed no transgene expression. Without being bound by theory, these data jointly suggest that the spinal parenchymal GFP expression (whether in neurons or projecting primary afferents) may be caused by retrograde or anterograde transgene expression, and not by an uptake of AAV9 into the spinal parenchyma from the intrathecal space. This observation is consistent with the data from other laboratories, which demonstrate potent α-motoneuron GFP expression after single intrathecal or cisternal AAV9-GFP injection in adult non-human primates or juvenile pigs. However, no interneuronal GFP expression is seen in the interneurons residing just in the close vicinity of GFP+ α-motoneurons (Meyer, et al. (2015). Improving single injection CSF delivery of AAV9-mediated gene therapy for SMA: a dose-response study in mice and nonhuman primates. *Molecular therapy: the journal of the American Society of Gene Therapy* 23: 477-487; Foust, et al. (2013). Therapeutic AAV9-mediated suppression of mutant SOD1 slows disease progression and extends survival in models of inherited ALS. *Molecular therapy: the journal of the American Society of Gene Therapy* 21: 2148-2159; Passini, et al. (2014). Translational fidelity of intrathecal delivery of self-complementary AAV9-survival motor neuron 1 for spinal muscular atrophy. Human gene therapy 25: 619-630; Bell, et al. (2015). Motor Neuron Transduction after Intracisternal Delivery of AAV9 in a Cynomolgus Macaque. *Human gene therapy methods* 26: 43-44).

In contrast, as described above, subpial AAV9 delivery was associated with potent transgene expression in the gray matter neurons (i.e., α-motoneurons and interneurons), and in virtually all descending motor axons and primary afferents of injected segments. These data clearly demonstrate that the pia mater represents the primary barrier preventing the penetration of AAV9 into other spinal cord compartments that are distant from the ventral and dorsal root entry zone. By bypassing the pial membrane and depositing the AAV9 into the subpial space a trans-parenchymal infection of white and gray matter can be effectively achieved in adult rodents or large animals.

Thus, the claimed methods and system can be used in subjects to increase axonal sprouting after spinal trauma by upregulating the expression level of neurotrophic genes in descending motor axons. Additionally, such local delivery of ASO enables a segment-restricted silencing of genes associated with the development of chronic pain or muscle spasticity to be targeted, but without a supraspinal side effect that is otherwise seen after intrathecal ASO delivery.

The potency of subpial-induced infection and the neuronal cell populations that are being infected in the spinal cord and brain in an adult animals has several potential clinical and experimental implications. First, in cases when a specific gene is to be silenced-downregulated, a single cervical subpial injection of the silencing AAV9 construct will lead to effective gene silencing in cervical neurons and glial cells, in descending motor axons throughout the whole length of spinal cord and in the majority of ascending sensory fibers. Given a well characterized neurodegenerative pattern in ALS patients and experimental models of ALS and which includes progressive degeneration of upper motor neuron and projecting descending motor axons, lower motor neuron and spinal interneurons, the ability to achieve widespread mutated gene silencing will likely provide a substantial advantage in achieving the most potent therapeutic effect. In addition, a single cervical subpial injection can be combined with one or more additional subpial injections into the lumbar enlargement to target the lumbar neuronal/glial population and/or with lumbar intrathecal injection to target α-motoneuronal pools throughout the thoracic and lumbar spinal cord. Second, increased expression of therapeutic genes (growth factors for example) associated with axonal sprouting can be readily achieved in descending motor tracts as well as ascending sensory fibers, and tested for its treatment potency in spinal trauma studies, for example. In this case the AAV9 vector can be administered from a single laminectomy site just at the injury epicenter with a subpial catheter advanced rostrally and caudally to target the distal end of severed motor axons and proximal ends of ascending sensory axons, respectively. Third, near complete descending motor tract labeling which can be achieved from cervical subpial AAV9-GFP injection will permit the study of axonal sprouting and synapse formation between labeled motor axons of the subject and spinally-grafted cells. Such data systematically characterizing the level of axonal sprouting and/or the development of synaptic contacts in cell-grafted large animal models of spinal injury are currently not available.

As described herein, an advantage of subpial AAV9 delivery, if compared to intrathecal delivery, appears to be superior spinal trans-parenchymal transgene expression. In addition, a comparable high level of transgene expression is achieved in fully adult rats or minipigs. Because the dimension of the spinal cord in adult 35-40 kg pigs is similar to that of humans, it is expected that a similar parenchymal AAV9 uptake will also be achieved in adult humans.

One of the relative limitations of the subpial delivery technique described herein is the requirement to perform local laminectomy to gain access to the dorsal surface of the subpially-injected spinal cord. The requirement for laminectomy can limit its repetitive use (which is in contrast to the potential for repetitive intrathecal delivery). However, the degree of transgene expression that can be achieved after subpial AAV9 delivery appears to balance, if not super pass, this limitation should a clear and more potent therapeutic effect be seen once subpially-based gene delivery is used in disease modifying studies. In addition, it has recently been determined that a continuing high level of spinal GFP expression remains at 12 months post-administration in the lumbar spinal cord in naïve-control rats. This would indicate that a single subpial delivery of a therapeutic gene can potentially lead to a long-lasting effect before additional gene delivery needs to be considered.

Figure 8:
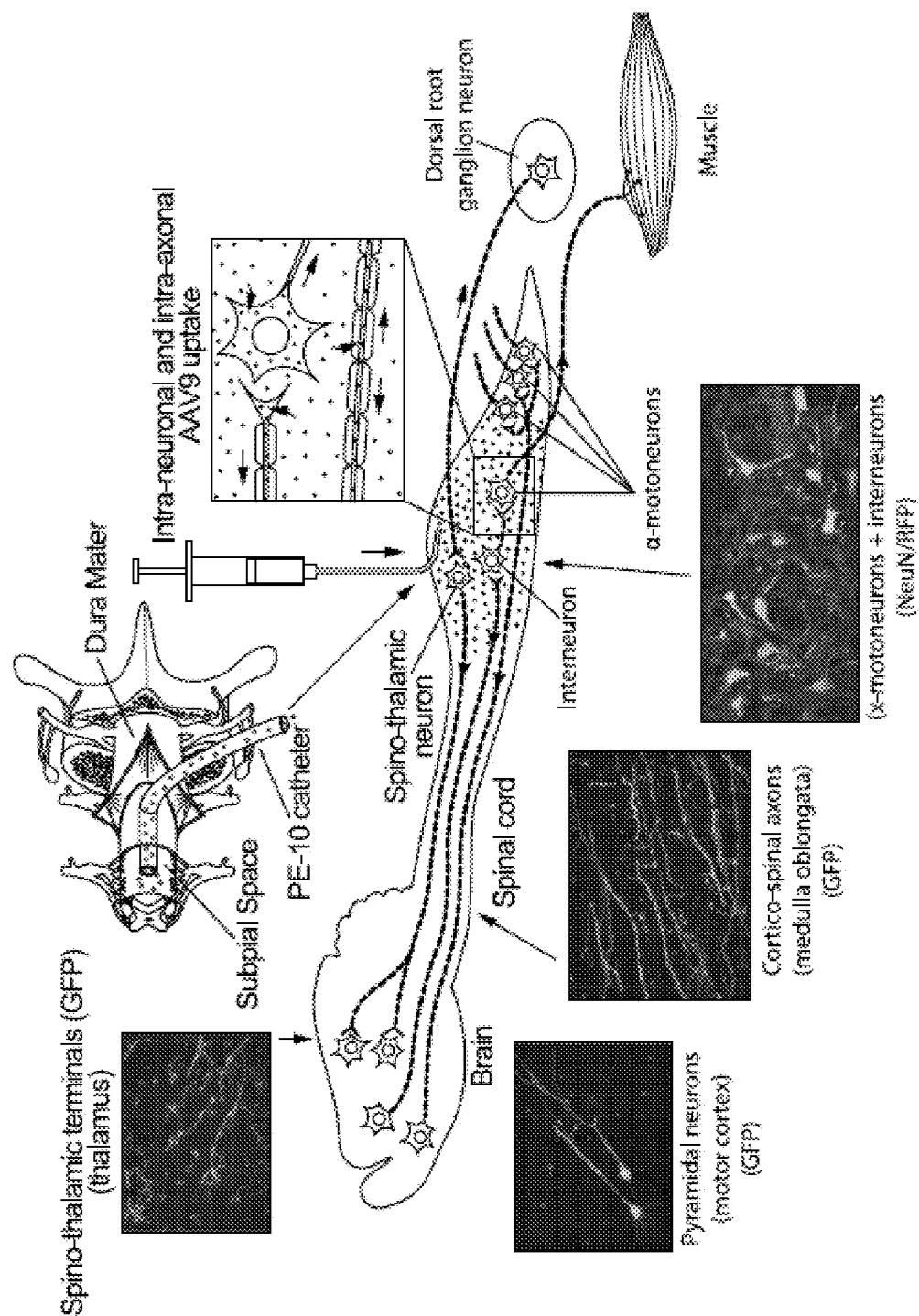
FIG. 8 is a pictorial schematic diagram showing subpial AAV9 delivery and resulting transgene (GFP) expression throughout the CNS after a single subpial AAV9-UBI-GFP injection. The AAV9-UBI-GFP virus is delivered into the subpial space using PE-10 catheter in an adult pig. Subpial delivery of AAV9-UBI-GFP leads to a diffusion and resulting uptake of virus into segmental neurons (i.e., interneurons and α-motoneurons) and ascending and descending axons which are trans-passing through the subpially-injected segments. Resulting transgene expression is then seen in: i) segmental neurons, ii) dorsal root ganglion cells (retrograde infection), iii) motor axons innervating skeletal muscles (anterograde infection), iv) pyramidal neurons in motor cortex (retrograde infection), and v) brain terminals of spinothalamic neurons (anterograde infection).

Using exemplary mammalian subjects (e.g., adult pigs and rats), the present invention demonstrates that the subpial spinal cord AAV9 delivery technique provided herein permits widespread transgene expression in spinal parenchyma, descending and ascending axons and does not require direct spinal cord tissue needle penetration (See FIG. 8). In addition to spinal regional transgene expression, robust retrograde expression in brain motor centers was seen. This technique can potentially be used in pre-clinical and human clinical studies targeted to upregulate or downregulate the gene of interest in specific spinal cord segments and/or in projecting motor and ascending sensory axons. The extent of transgene expression in these exemplary adult animals suggests that present invention may be successfully used in the adult patient population to target a variety of spinal neurodegenerative disorders and/or CNS-related disorders. Exemplary neurodegenerative disorders, CNS-related disorders, diseases, or injuries include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amyotrophic lateral sclerosis (ALS), Huntington's disease, Alzheimer's disease, Parkinson's disease, Parkinson's-plus diseases (e.g., multiple system atrophy, progressive supranuclear palsy, and corticobasal degeneration), surgical resection, spinal cord injury or trauma, CNS injury resulting from tumor resection, transverse myelitis, optical myelitis, Guillain-Barré syndrome (GBS), stroke, traumatic brain injury, post radiation injury, neurologic complications of chemotherapy, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, glossopharyngeal neuralgia, myasthenia gravis, epilepsy, Bell's palsy, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, and chronic pain syndrome.

In some embodiments, the AAV compositions are formulated to reduce aggregation of AAV particles in the composition, particularly where high AAV concentrations are present (e.g., ~$10^{13}$ GC/ml or more). Methods for reducing aggregation of AAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active AAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The agents, compositions, and/or systems described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include compositions including the AAV for administration, as described herein, along with instructions describing the intended application and the proper use of the composition. In certain embodiments, the kits may further include a separate container containing a guiding tube (e.g., 18 or 23G) bended at 90° and a catheter (e.g., PE-5 or PE-10) suitable for a particular application and for a method of subpial administration of the composition. Kits for research purposes may contain the components in appropriate concentrations or quantities for running various experiments. The kit may further include one or more or all of the components required to administer the composition subpially to a subject, such as a syringe, caudal and/or cranial spinal clamps, XYZ manipulator, etc.

As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The following examples are intended to illustrate but not limit the invention.

Example 1

Materials and Methods

Animals and General Surgical Preparation—

Adult Sprague-Dawley rats (male and female, 250-350 grams; n=16) or adult minipigs resulting from cross-breeding of Minnesota and Gottingen strains (both sexes; 30-40 kg; n=6) were used. Rats were anesthetized with 5% isoflurane and maintained at 2-3% of isoflurane during surgery depending on breathing rate and paw pinch response. The back of the rat was then shaved and cleaned with 2% chlorohexadine. After skin incision, the paravertebral muscle surrounding the cervical, thoracic or lumbar spinal vertebrae was removed and animals mounted into a spinal immobilization frame (Stoelting) using Cunningham's spinal clamps as previously described (Kakinohana, et al. (2004). Region-specific cell grafting into cervical and lumbar spinal cord in rat: a qualitative and quantitative stereological study. *Experimental neurology* 190: 122-132). To expose the spinal cord a dorsal laminectomy of corresponding vertebra was performed using a dental drill. The dura was then cut opened using a scalpel blade.

Minipigs were premedicated with intramuscular azaperonum (2 mg/kg) and atropine (1 mg/kg; Biotika, SK) and then induced with ketamine (20 mg/kg; IV). After induction, animals were intubated with a 2.5F tracheal tube. Anesthesia was maintained with 1.5% isoflurane in 50%/50% air/oxygen mixture at a constant 2 L/min flow rate. Oxygen saturation was monitored throughout the procedure using a pulse oximeter (Nellcor Puritan Bennett Inc., Ireland). After induction of anesthesia, animals were placed into a spinal immobilization apparatus as described previously (Usvald, et al. (2010). Analysis of dosing regimen and reproducibility of intraspinal grafting of human spinal stem cells in immunosuppressed minipigs. *Cell transplantation* 19: 1103-1122). A dorsal laminectomy of Th5 or L2-L4 vertebrae, corresponding to Th5 and L3-L6 spinal segments, respectively, was then performed and epidural fat removed using cotton swabs. The dura was cut open and secured to the surrounding tissue using 6.0 Proline (FIGS. 1C-1E).

Placement of Subpial Catheter and Subpial AAV9 Injection—

Figure 1B:
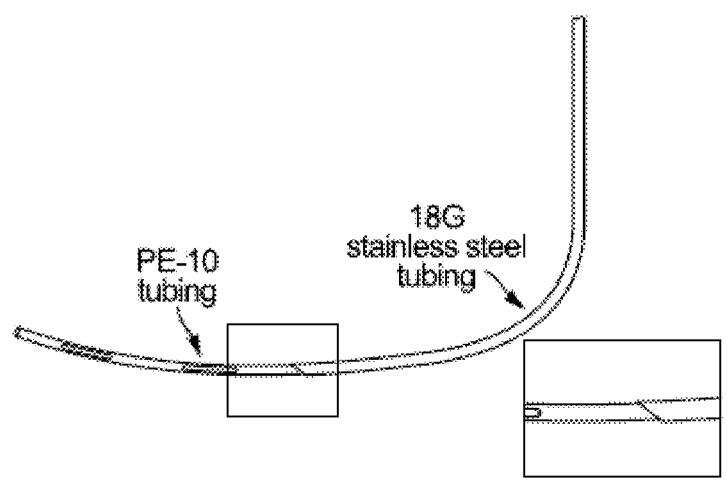
Figure 1C:
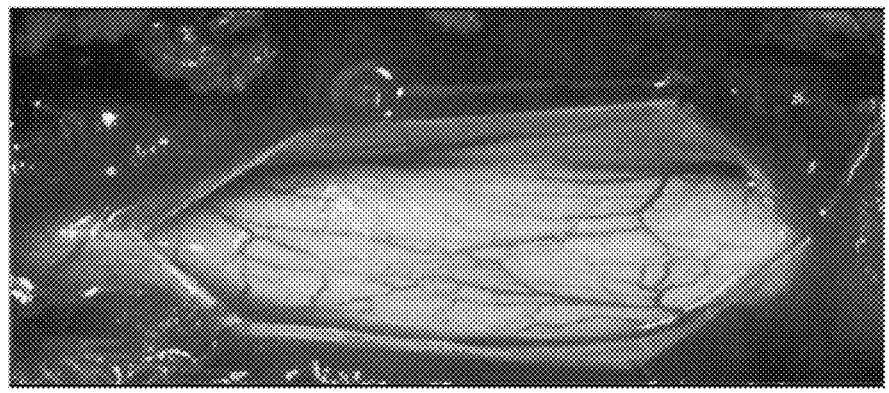
Figure 1D:
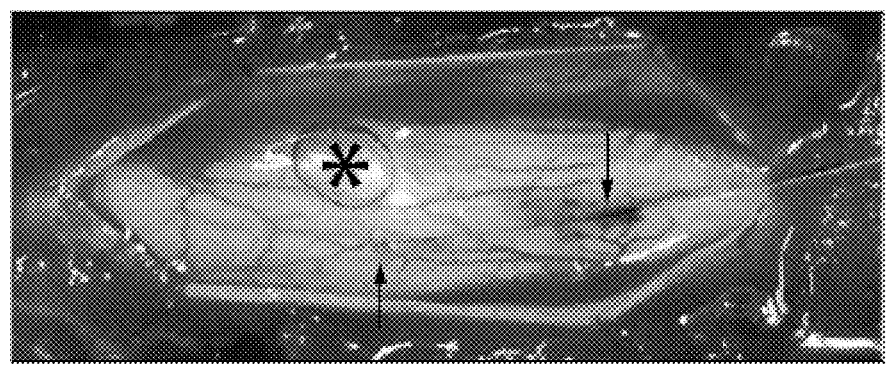
Figure 1E:
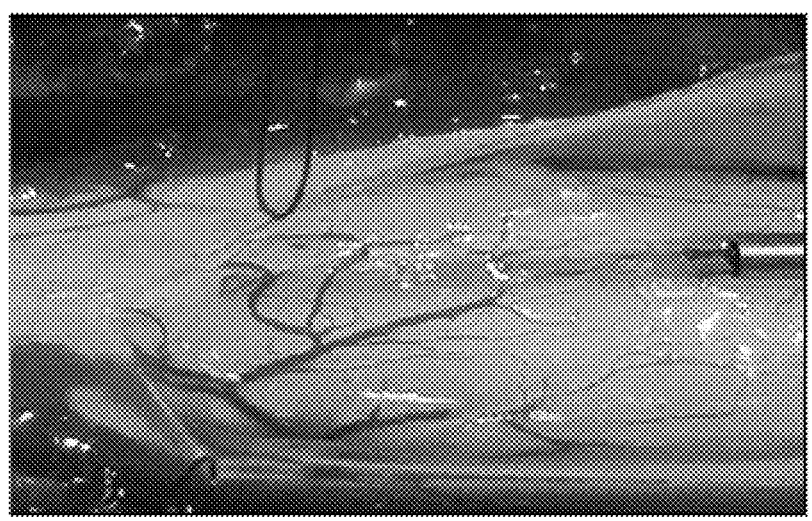

To place the subpial catheter, an L-shape catheter guiding tube (18 or 23G) was constructed (FIG. 1B). The guiding tube was mounted into an XYZ (Stoelting) manipulator and advance to the surface of the exposed spinal segment. A 30G needle previously bent into 45° was used to puncture the pia. The subpial catheter (PE-10 for pig and PE-5 for rat) was then advanced into the subpial space from the guiding tube by manually pushing the catheter from the other end of the guiding tube. In rats, the catheter was advance into the subpial space for about 1-1.5 cm, and in pigs for about 3-6 cm. The virus was then injected into the subpial space over 3 min using a 50 or 250 µl Hamilton syringe. After injection the catheter was removed, dura closed using 6.0 Proline (dura is closed in pig only), and animals allowed to recover.

Preparation of AAV9 for In Vivo Injection—

1.2 kb ubiquitin-C (UBC) promoter was made by oligonucleotide synthesis, linked with either eGFP or DsRed (RFP) and SV40 polyA signal, and cloned into a self-complementary double-strand DNA genome AAV (scAAV) vector plasmid (Xu, et al. (2012). In vivo gene knockdown in rat dorsal root ganglia mediated by self-complementary adeno-associated virus serotype 5 following intrathecal delivery. PloS one 7: e32581). Helper virus-free scAAV9 vectors expressing either eGFP or RFP driven by UBC promoter were produced by transient transfection of HEK293T cells with the vector plasmid, pRep2-Cap9 and pAd-Helper plasmids (Xiao, et al. (1998). Production of high-titer recombinant adeno-associated virus vectors in the absence of helper adenovirus. *J Virol* 72: 2224-2232). Plasmid pRep2-Cap9 was obtained from the Vector Core of U. Penn. AAV vectors in the cell lysates prepared at 72 hrs after transfection were purified as previously described and titered by Q-PCR (Xu, et al., supra). The final titers were adjusted to $1.0 \times 10^{13}$ genome copies per ml (gc/ml). Just before injection the virus was mixed with dextran (10,000 MW) 1:1 to a final dextran concentration of 2.5%. The volume subpial injectate was 30 µl in rats and 200 µl in pigs.

Perfusion Fixation, Postmortem In Situ GFP Fluorescence Imaging and Immunofluorescence Staining of Spinal Cord and Brain Sections—

Animals (rats and pigs) were deeply anesthetized with pentobarbital and transcardially perfused with 200 ml (rat) or 2000 ml (pig) of heparinized saline followed by 250 ml (rat) or 4000 ml (pig) of 4% paraformaldehyde in PBS. The spinal cords and brains were dissected and post-fixed in 4% formaldehyde in PBS overnight at 4° C. and then cryoprotected in 30% sucrose PBS until transverse or longitudinal sections (30-µm-thick) were cut on a cryostat and stored in PBS. Before sectioning the whole spinal cord was imaged in situ using an IVIS Spectrum optical imaging system (Xenogen, Alameda, Calif.). Sequences were acquired at excitation wavelength 465 nm and emission wavelength 520 nm. Medium binning was used, and the exposure time was 3 seconds. Images were analyzed using Living Image 4.3.1 (Xenogen, Alameda, Calif.) software. The signals were calculated using fixed volume ROIs. Prepared sections were immunostained overnight at 4° C. with the following primary antibodies made in PBS with 0.2% Triton X-100: rabbit anti-glial fibrillary acidic protein (GFAP; 1:500, Origene, Rockville, Md., USA) and mouse anti-neuronal nuclei antigen (NeuN, 1:1000, Chemicon). After incubation with primary antibodies, sections were washed three times in PBS and incubated with fluorescent-conjugated secondary donkey anti-rabbit and donkey anti-mouse antibodies (Alexa Fluor 488, 546 or 647, 1:1000, Invitrogen), respectively, and DAPI for general nuclear staining. Sections were then mounted on slides, dried at room temperature and covered with a Prolong anti-fade kit (Invitrogen). Fluorescence images were captured using a Zeiss Imager M2 microscope and confocal images were taken using an Olympus FV1000 microscope.

The consistency, high level of spinal parenchymal transgene expression, and feasibility of this approach represent a major technological improvement over current approaches, with a potential direct clinical application aimed at spinal gene upregulation or silencing in general. Currently used approaches employ spinal intrathecal or invasive direct intraparenchymal AAV injection with its apparent limitations such as a low level of parenchymal transgene expression or its invasive nature required to achieve a more robust infection effect. In addition, this approach provides an unparalleled level of motor and sensory fibers labeling at segments distant from the site of AAV9 delivery making it a very robust tool to study the extent of synaptic connectivity and to identify factors (i.e., genes, neurothrophic factors) that regulate axonal sprouting in targeted spinal segments in both rodents and large animal species.

An example demonstrating the principle of spinal subpial AAV9 delivery and resulting regional parenchymal expression as well as axonal labeling in segments distant from the site of AAV9 delivery in the adult pig at 2 months post-AAV9 delivery is provided herein.

Example 2

Parenchymal AAV9-Mediated Transgene Expression after Single Supial Bolus

Figure 1J:
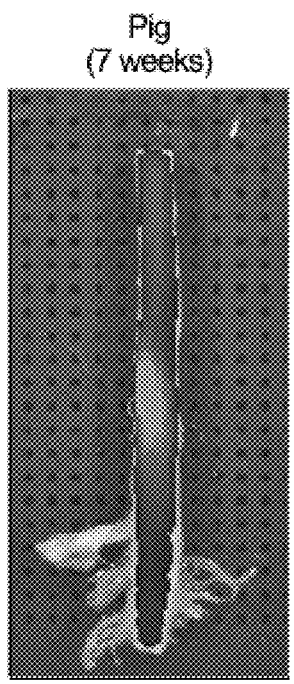
Figure 1J:
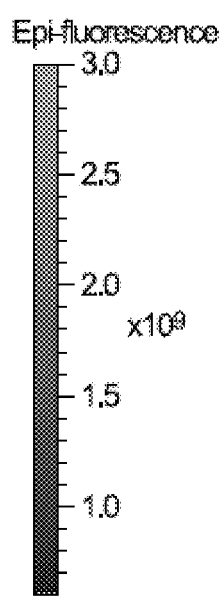
Figure 1J:
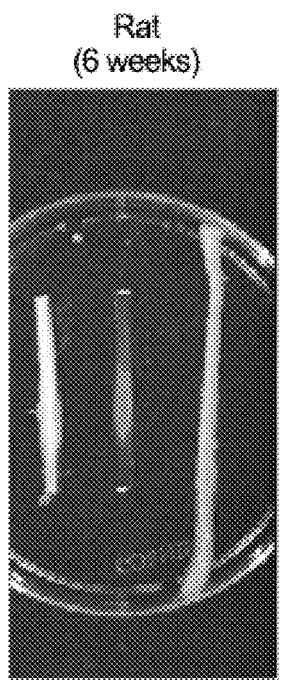
Figure 1J:
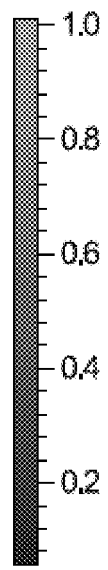
Figure 1J:
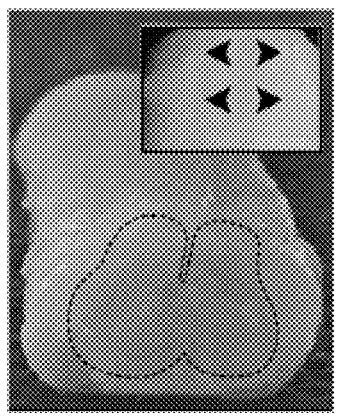
Figure 1J:
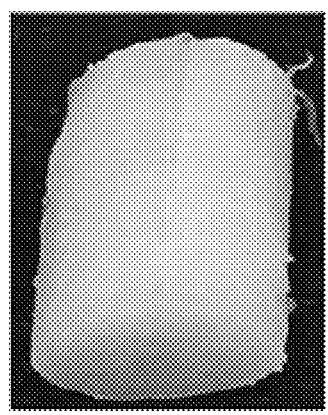
Figure 1J:
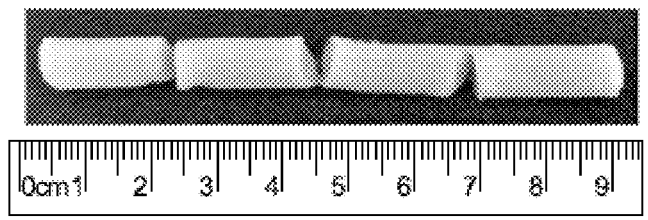
Figure 2A:
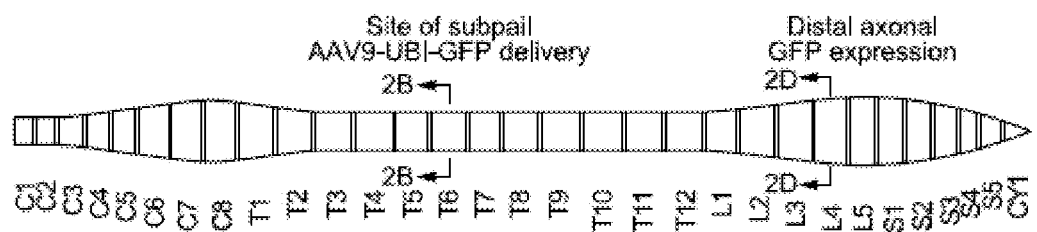
FIGS. 2A-2D are pictorial diagrams showing insertion of the PE-10 catheter into the subpial space and GFP expression throughout the spinal parenchyma and in axons projecting distally from AAV9 injected segments.
Figure 2B:
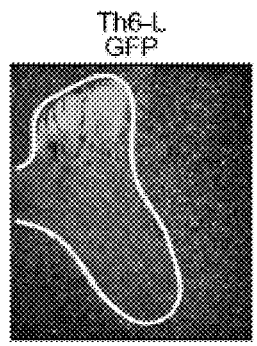
Figure 2C:
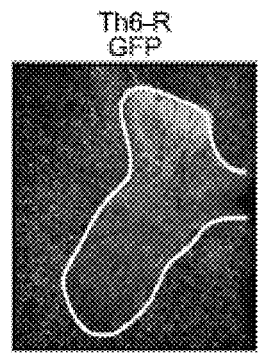
Figure 2D:
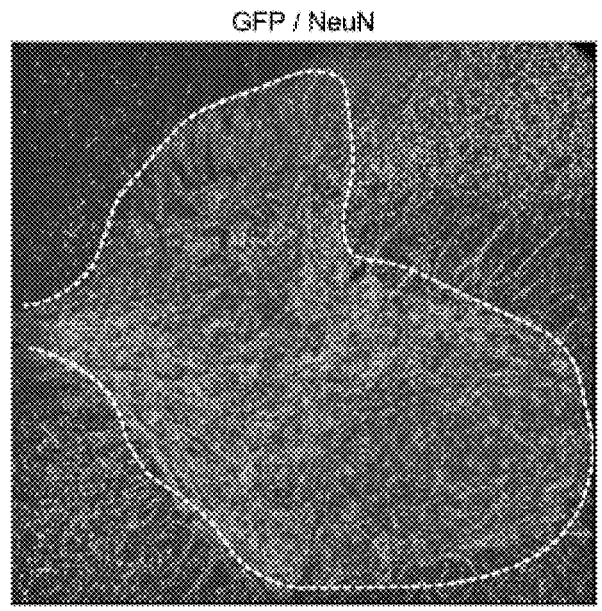

Initially, the potency of single bolus subpial AAV9-UBI-GFP or AAV9-UBI-RFP delivery in rats and pigs was tested. Animals received 20 µl (rat) or 200 µl (pig) of AAV9 vector in 2.5% dextran solution delivered into subpial space of cervical (C4-6), thoracic (Th6-9) or lumbar (L2-L5) segments. At 6-8 weeks after AAV9 delivery spinal cords were dissected from 4% paraformaldehyde-fixed animals and imaged in situ using Avis fluorescence system. Transverse or horizontal spinal cord sections were then cut from AAV9-injected segments and analyzed for the presence of GFP or RFP and co-stained with neuronal (NeuN) and glial (GFAP) antibodies. In both rat and pig spinal cord an intense GFP or RFP expression was seen on the surface of the spinal cord and was readily identified by visual inspection as yellow-green or red areas. FIGS. 1H and 1J show the presence of RFP (red color) in transversely cut pig spinal cord and in the ventral roots (FIG. 1H, insert) in comparison to naive spinal cord (FIG. 1I). Correspondingly, the spinal surface densitometric analysis of AAV9-UBI-GFP-injected animals showed a wide spread of GFP signal extending for up to 5-10 cm from the epicenter of subpial AAV9 delivery (FIGS. 1F and 1G).

Using horizontally cut thoracic sections taken from pigs previously injected subpially with AAV9-UBI-RFP in the mid-thoracic level (the same spinal cord as shown in FIG. 1H), extensive parenchymal RFP expression was seen. The RFP expression was readily identified in the majority of interneurons and α-motoneurons and extended throughout 4-6 spinal segments (FIGS. 3A and 3B). Similarly, intense RFP expression in axo-dendritic arbor was seen throughout the whole RFP-expressing gray matter (FIGS. 3A and 3B, white asterisks).

Analysis of transverse spinal cord sections taken from the epicenter of subpial AAV9 injection confirmed an intense RFP expression throughout the white and gray matter. In white matter, a punctate-like RFP expression was seen in the majority of transversally-cut axons (FIG. 3C, white asterisks, box inserts) and were identified in dorsal, lateral and ventral funiculi (FIG. 3C, DF, LF, VF; box inserts). In the gray matter, numerous interneurons distributed between laminae I-IX and ventral α-motoneurons in ventral horns showed intense RFP expression in soma and in axo-dendritic arbor. A high density of RFP expression was also seen in the terminal boutons thorough the gray matter (FIGS. 3D-3G). Similarly, confocal analysis showed the presence of RFP signal in astrocytes (FIG. 3C, insert: RFP/GFAP).

A similar neuronal GFP expression pattern was seen in the rat lumbar spinal cord after subpial AAV9-UBI-GFP injection at the L1-2 level. A high density of GFP+ neurons throughout the L1-L5 lumbar segments and localized in the whole gray matter between laminae I-IX was identified (FIGS. 9A-9D).

Example 3

GFP Expression in Distant Spinal Segments

Next, the extent of descending spinal tract GFP expression in lumbar spinal cord was characterized after subpial injection of AAV9-UBI-GFP into the subpial space of mid-thoracic (Th6-7) or lower cervical segments in both rats and pigs. At 3-6 weeks after subpial AAV9 delivery, an intense GFP expression was seen throughout the whole lumbar spinal cord. Using transverse lumbar (L2-L6) spinal cord sections taken from pigs high intensity GFP expression in transversely-cut axons in the lateral and ventral funiculi was readily identified without additional GFP immunostaining (FIG. 4A, white asterisks). In these regions a similar density of GFP+ axons was seen throughout the whole white matter. In comparison to lateral and ventral funiculi, a relatively lower number of GFP+ axons was seen in the dorsal funiculi. (FIG. 4A, DF). Consistent with the degree of axonal labeling seen in the white matter of lateral and ventral funiculi a dense network of GFP+ axons terminating in the gray matter was seen (FIGS. 4A and 4B). These axons were identified between laminae III-X. Only few GFP+ axons in the lamina I-III were seen. High power confocal microscopy showed a high density of fine GFP+ axons with numerous terminal boutons in the gray matter (FIG. 4C).

Figure 9A:
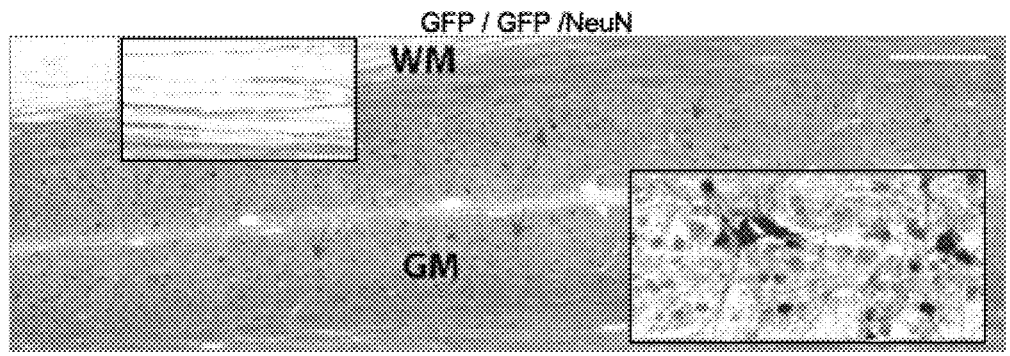
FIGS. 9A-9F are pictorial diagrams showing effective parenchymal AAV9-mediated transgene expression after single bolus lumbar subpial AAV9-UBI-GFP injection in adult rat.
Figure 9B:
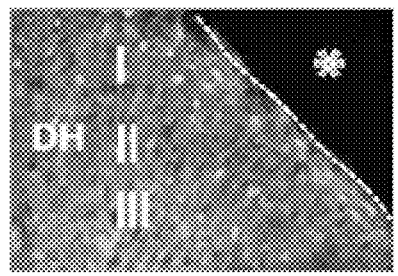
Figure 9C:
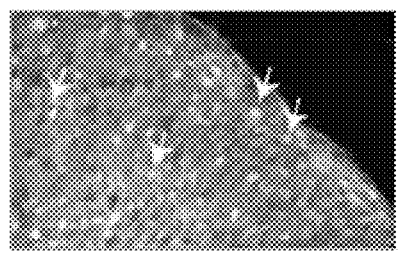
Figure 9D:
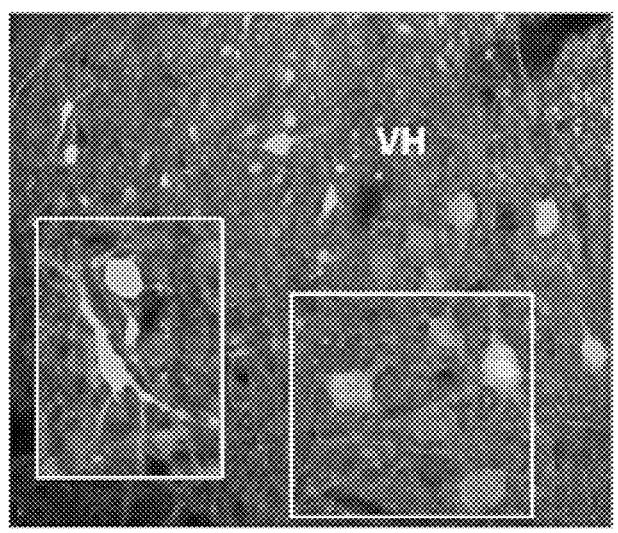
Figure 9E:
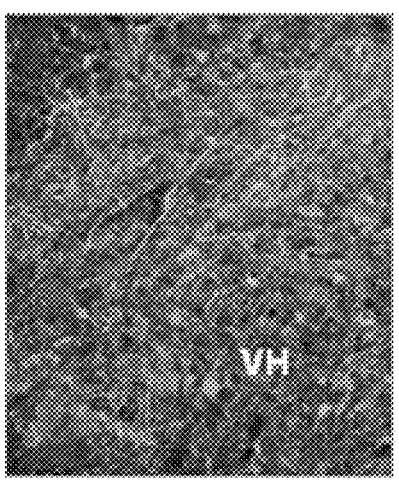
Figure 9F:
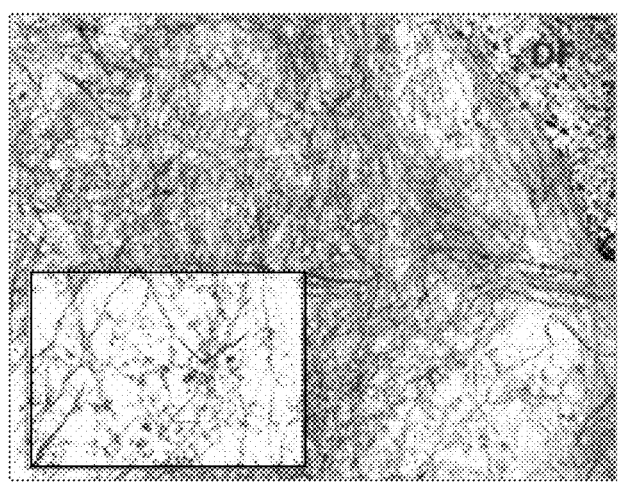

A comparable GFP expression pattern in descending motor axons in lumbar gray matter was seen in rats previously receiving upper cervical subpial injection of AAV9-UBI-GFP (FIGS. 9E and 9F).

Example 4

Figure 5A:
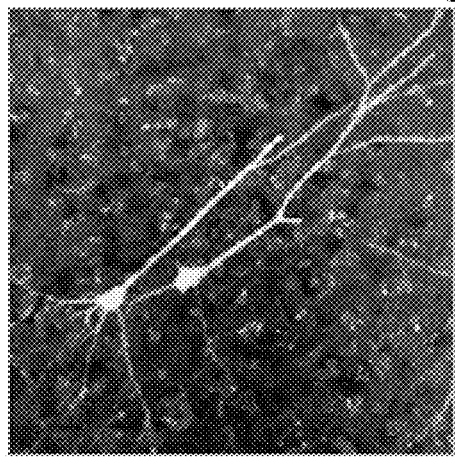
FIGS. 5A-5L are pictorial diagrams showing retrograde transport-mediated GFP expression in brain motor centers after subpial mid-thoracic AAV9 delivery in adult pig.
Figure 5B:
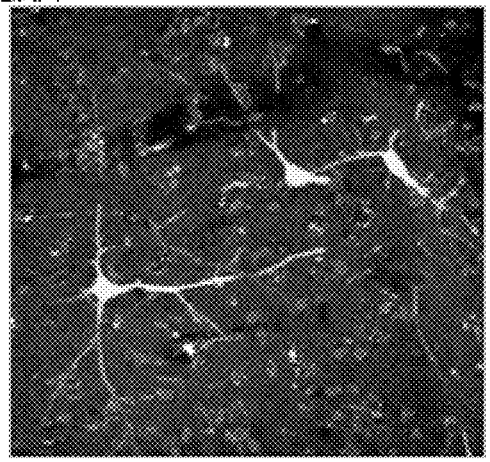
Figure 5C:
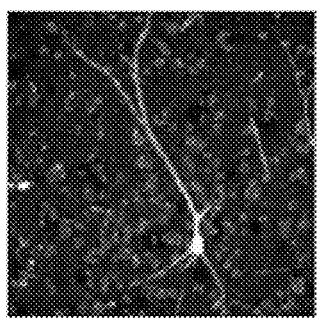
Figure 5D:
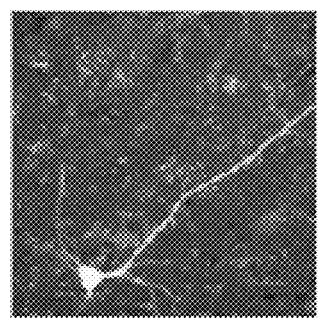
Figure 5E:
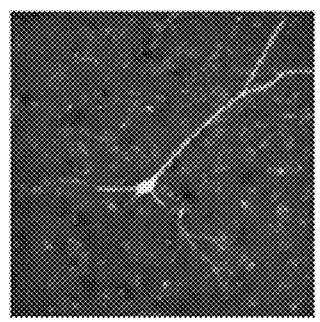
Figure 5F:
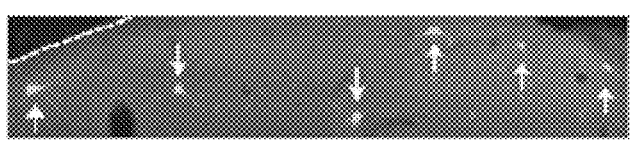
Figure 5K:
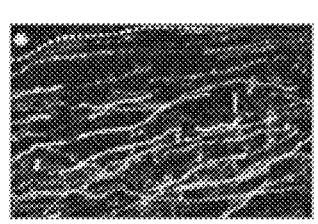
Figure 5G:
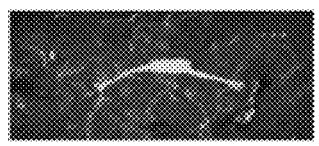
Figure 5I:
Figure 5L:
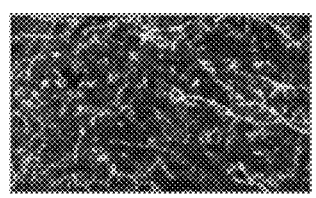
Figure 5H:
Figure 5J:

Retrograde Transgene Expression in Brain Motor Regions after Spinal Subpial Delivery Analysis of transgene (GFP) expression in brain motor centers (motor cortex, nucleus ruber and formatio reticularis) at six weeks after subpial AAV9-UBI-GFP delivery in pigs showed intensely GFP-labeled pyramidal neurons in the motor cortex (FIGS. 5A-5E). Similarly, numerous GFP+ neurons localized in the brain stem were identified (FIGS. 5F-5J). Consistent with the presence of GFP+ neurons in the motor cortex, a high number of GFP+ corticospinal axons in the ventral region of the medulla oblongata (medullary pyramids) was seen (FIG. 5K). In addition, a high density of anterogradely labeled GFP+ spinoreticular terminals was seen throughout the reticular formation (FIG. 5L) as well as spinothalamic terminals in the thalamic nuclei (not shown).

Figure 6A:
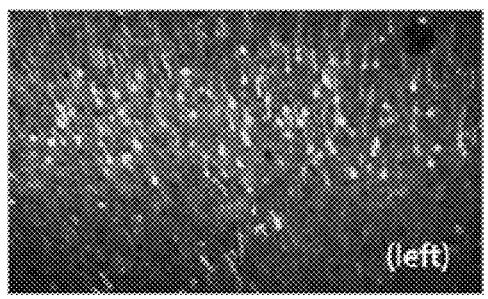
FIGS. 6A-6G are pictorial diagrams showing retrograde-transport-mediated GFP expression in brain motor centers after subpial cervical AAV9 delivery in adult rat.
Figure 6B:
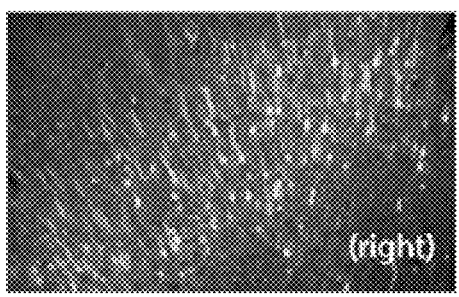
Figure 6C:
Figure 6D:
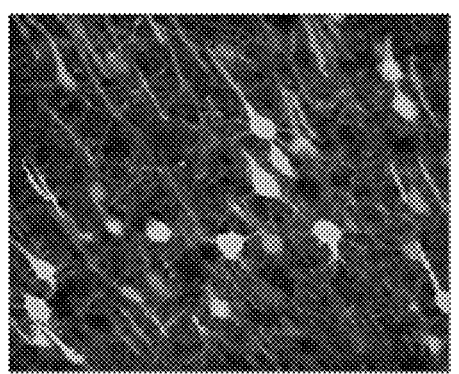
Figure 6E:
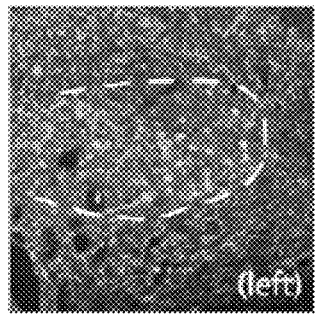
Figure 6F:
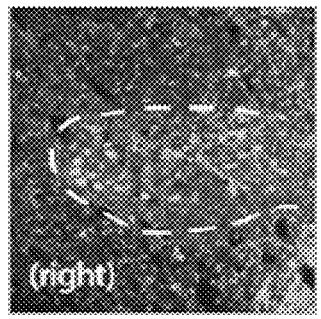
Figure 6G:

Comparably, as seen in pigs, a high density of GFP+ pyramidal neurons localized bilaterally in motor cortex was seen in rats (FIGS. 6A-6D). A similar high level of GFP expression was also seen in the nucleus ruber and was easily identified by the presence of bilaterally localized GFP+ nuclear-neuronal clusters (FIGS. 6E-6G).

Example 5

Figure 7A:
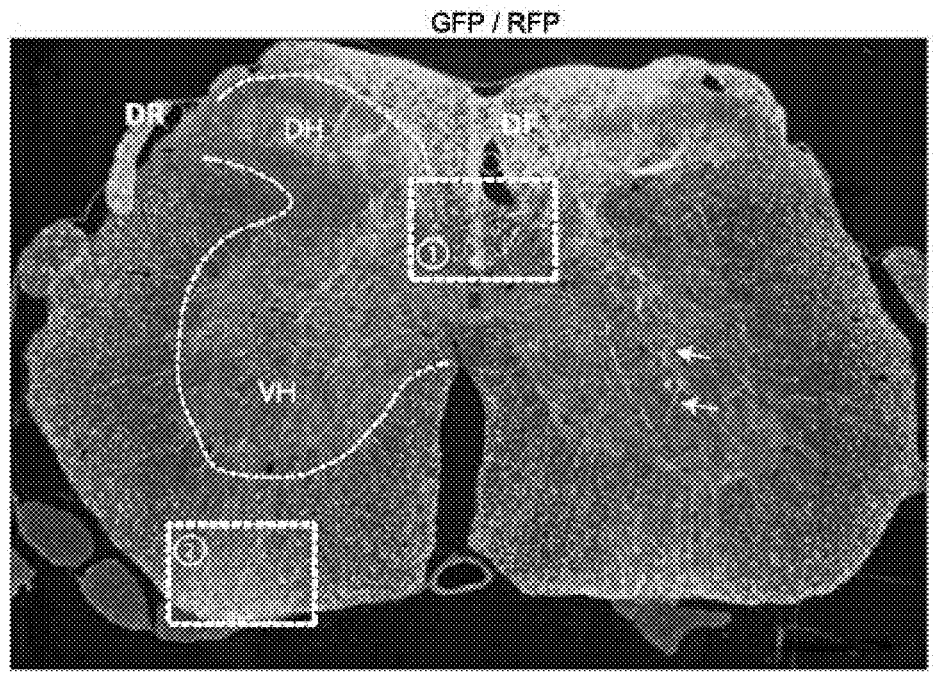
Figure 7B:
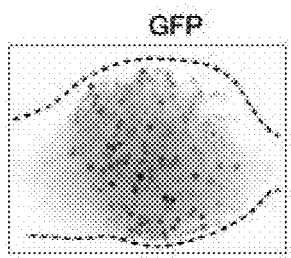
Figure 7C:
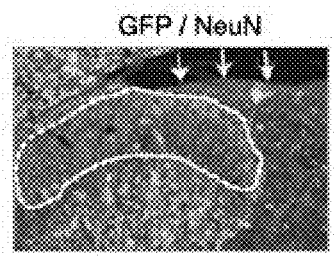
Figure 7D:
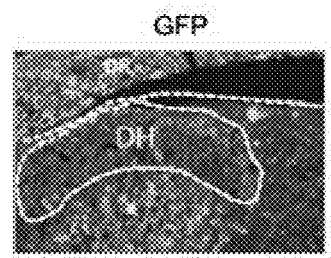
Figure 7G:
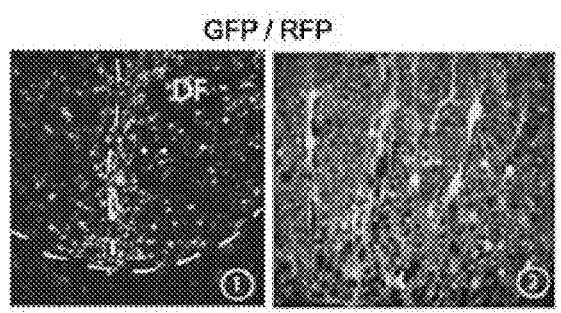
Figure 7G:
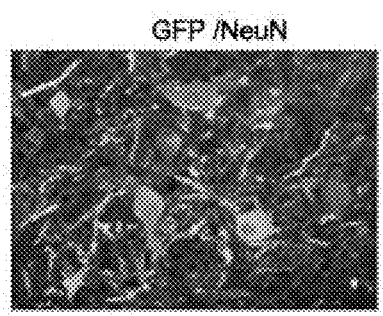

Differential Regional Spinal Transgene Expression after Intrathecal Vs. Subpial AAV9 Delivery The distribution of spinal transgene expression was then compared once the AAV9 was injected into the lumbar (L1-L2) intrathecal space (AAV9-UBI-GFP) and into the subpial space of thoracic Th7 segment (AAV9-UBI-RFP) in the same animal (rat). Subpial AAV9 injection was performed three weeks after lumbar intrathecal AAV9 injection and the expression pattern was analyzed in the transverse lumbar spinal cord sections at three weeks after subpial AAV9 injection. Intrathecal injection of AAV9-UBI-GFP led to intense GFP expression in the dorsal funiculus, primary afferents in dorsal horn (lamina and in the medial part of lamina V-VII. Several GFP+ Ia afferents terminating in the ventral horn in the vicinity of CHAT+ α-motoneurons were also identified. Consistent with a high GFP expression in primary afferents, a high number of GFP+ neurons were found in dorsal root ganglion cells (FIG. 7B). A clear presence of increased GFP expression was also consistently seen around the ventral root entry zone (FIGS. 7A and 7F). In this region, several GFP expressing glial cells were seen. Similarly, few GFP+ cells were identified in the dorsal root entry zone. In the ventral gray matter, some α-motoneurons showed GFP expression (FIG. 7G). Except for these regions and cell groups which showed GFP expression, near complete lack of neuronal or glial GFP expression was seen in other deeper regions of the gray matter including dorsal horn, intermediate zone and in white matter of lateral and ventral funiculi (FIG. 7A). Interestingly, even the neurons localized in the superficial dorsal horn and which reside in a close vicinity to the intrathecal space (but separated by pia mater) showed a complete lack of GFP expression (FIGS. 7C and 7D).

In contrast to the GFP expression pattern seen after intrathecal AAV9-UBI-GFP delivery, the RFP expression resulting from cervical subpial AAV9 injection showed a substantially different regional expression pattern if analyzed in the same lumbar spinal cord sections. The dsRED expression was identified in the majority of axons in white matter and was present in lateral and ventral funiculi. Numerous axons projecting into the gray matter of the dorsal horn, intermediate zone (Lamina VII) and ventral horn were also seen (FIG. 7A). Confocal microscopy showed that virtually all RFP+ fibers either in the white or gray matter were GFP negative. Interestingly, numerous RFP+ corticospinal axons residing on the base of dorsal funiculi were found in close vicinity of the GFP-labeled primary afferents but no colocalization of RFP+ GFP was identified in either of these fibers (FIG. 7E).

Example 6

Identification of GFP-Labeled Cells at 3-6 Months Post Delivery

To deliver cells into spinal subpial space the dorsal surface of spinal cord is exposed by laminectomy and dura is cut opened (see, FIG. 1C). A PE-5 or PE-10 (polyethylene) catheter is then placed into subpial space using an XYZ manipulator (FIGS. 1D and 1E). Cells are then injected into subpial space using a digital injector and 1 cc syringe. Cells are delivered at densities ranging between 10,000-80,000 cells/microliter. The total of 10-1000 micoliters of cell suspension can be delivered in rat or pig.

Figure 10A:
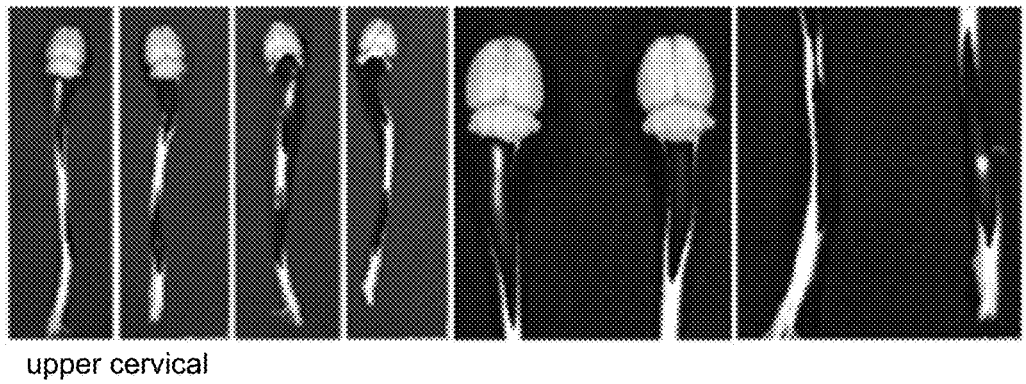
FIGS. 10A-10C are pictorial diagrams showing survival migration of human fetal spinal stem cells at six months after subpial (cervical+ lumbar) cell delivery in immunodeficient rat. At intervals 3-6 months after cell delivery GFP-labeled cells are identified on the surface of spinal cord (FIG. 10A) and in deep spinal white and gray matter (FIGS. 10B and 10C) in immunodeficient rat receiving one cervical and one lumbar subpial injection of human fetal spinal cord-derived GFP-tagged neural precursors.
Figure 10B:
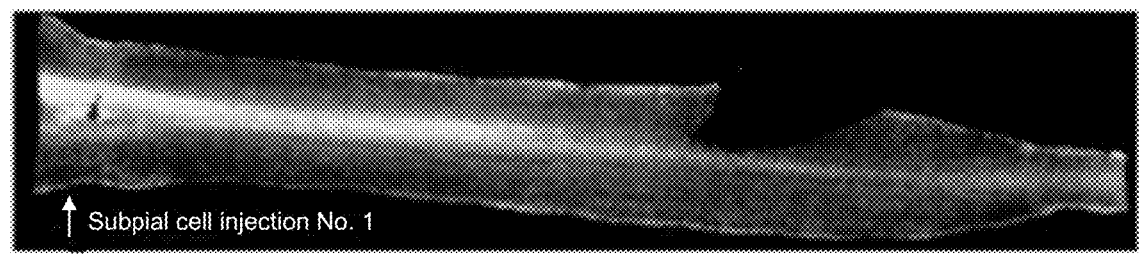
Figure 10B:
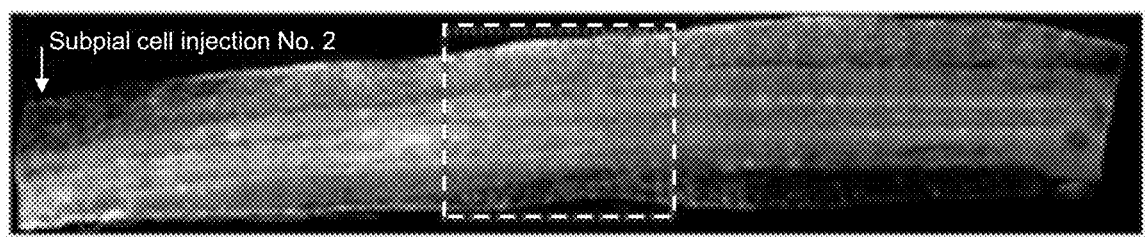
Figure 10C:
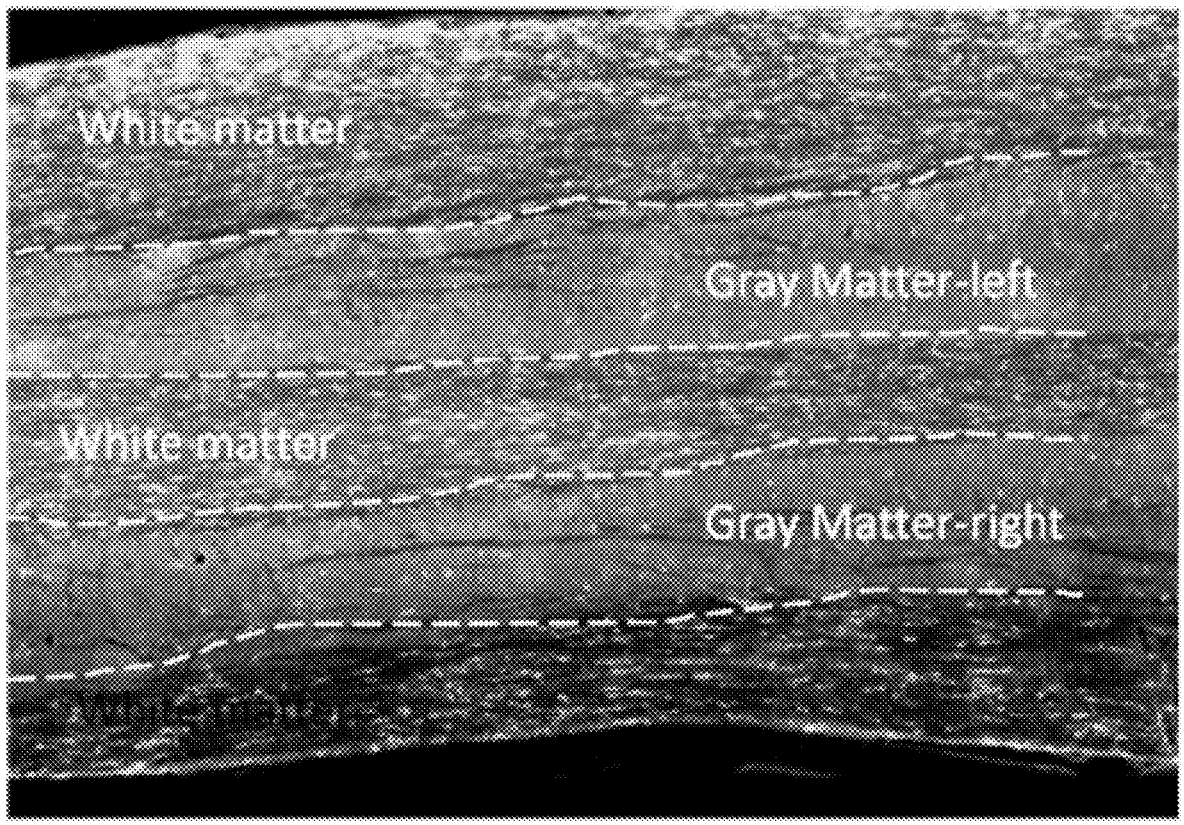
Figure 11:
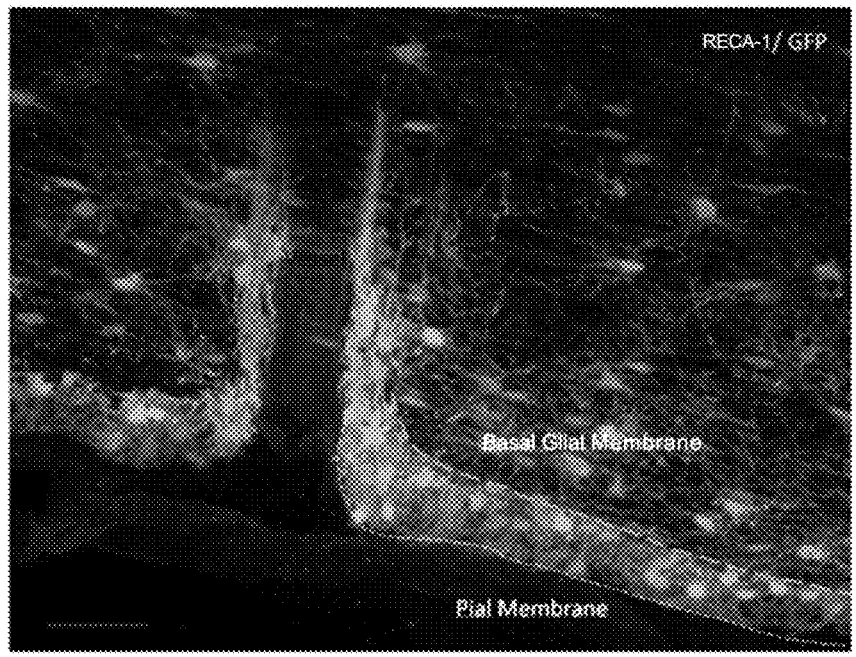
FIG. 11 is a pictorial diagram showing higher density of GFP+ cells are identified to reside in subpial space.
Figure 12:
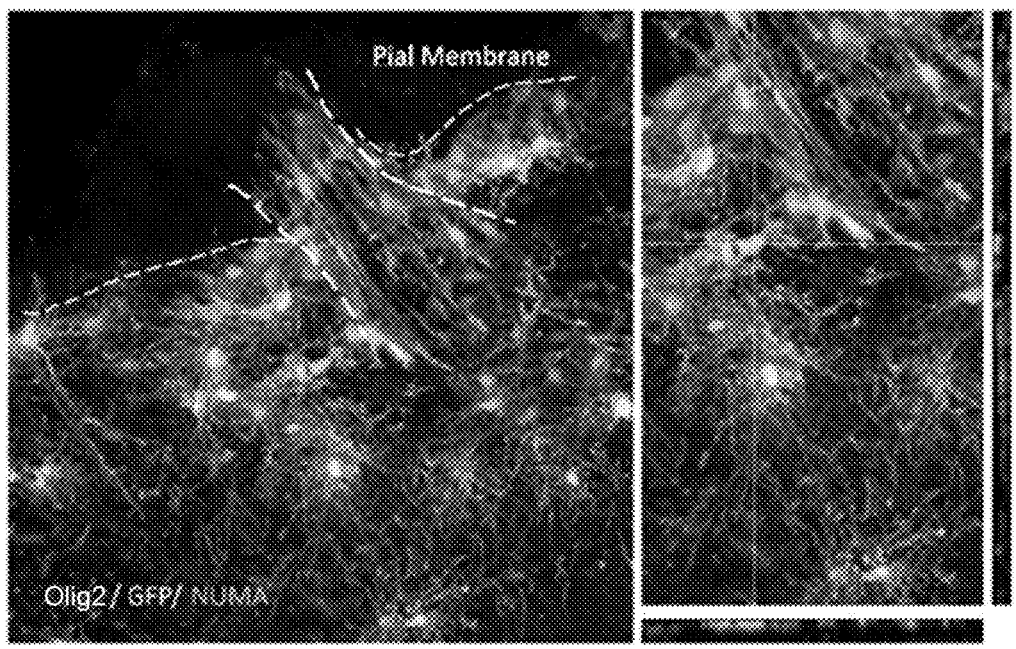
FIG. 12 is a pictorial diagram showing higher density of GFP+ cells are identified to reside in subpial space.

At intervals of 3-6 months after cell delivery GFP-labeled cells are identified on the surface of spinal cord (FIG. 10A) and in deep spinal white and gray matter (FIGS. 10B and 10C) in immunodeficient rat receiving one cervical and one lumbar subpial injection of human fetal spinal cord-derived GFP-tagged neural precursors. Higher density of GFP+ cells are identified to reside in subpial space (FIGS. 11 and 12).

By delivering neural precursors into spinal subpial space we were able to achieve a wide spread cell repopulation of entire spinal cord by injected cells in rat. We have demonstrated that only 2 subpial injections (one cervical and lumbar) are sufficient to provide near complete repopulation of spinal cord white and in part gray latter by injected cells. In addition a significant number of cells which migrated into brain stem is also seen.

Example 7

Subpial AAV9 Delivery in Adult Mice

Because of the wide range of transgenic mouse models of neurodegenerative diseases, there is a strong desire for the development of a potent central nervous system (CNS)-targeted vector delivery technique in adult mice. Such a technique permits the study of the effect of specific gene silencing (e.g., using shRNA) or upregulation using cell-non-specific (e.g., cytomegalovirus-CMV or Ubiquitin) or cell-specific (e.g., synapsin or glial fibrillary acidic protein (GFAP)) promoters during early postnatal development or under diseased conditions. Accordingly, the present study describes the development of a spinal subpial vector delivery technique to permit safe and effective spinal AAV9 delivery in adult C57BL/6J mice.

In spinally immobilized and anesthetized mice, the pia mater (cervical 1 and lumbar 1-2 spinal segmental level) was incised with a sharp 34 G needle using an XYZ manipulator. A second XYZ manipulator was then used to advance a blunt 36G needle into the lumbar and/or cervical subpial space. The AAV9 vector (3-5 µL; $1.2 \times 10^{13}$ genome copies (gc)) encoding green fluorescent protein (GFP) was then injected subpially. After injections, neurological function (motor and sensory) was assessed periodically, and animals were perfusion-fixed 14 days after AAV9 delivery with 4% paraformaldehyde. Analysis of horizontal or transverse spinal cord sections showed transgene expression throughout the entire spinal cord, in both gray and white matter. In addition, intense retrogradely-mediated GFP expression was seen in the descending motor axons and neurons in the motor cortex, nucleus ruber, and formatio reticularis. No neurological dysfunction was noted in any animals. These data show that the subpial vector delivery technique can successfully be used in adult mice, without causing procedure-related spinal cord injury, and is associated with highly potent transgene expression throughout the spinal neuraxis.

General Animal and Surgical Preparation—

Before starting the surgical procedure, the virus (AAV9-UBI-GFP; 5 µL aliquots) was thawed, and a 5% dextran (10,000 MW) solution was prepared by mixing dextran powder in distilled water. The virus solution was then mixed with 5% dextran solution 1:1 to a final dextran concentration of 2.5%. The virus solution was stored on ice at 4° C. Adult C57BL/6J mice (male and female, 20-30 g) were anesthetized using 5% isoflurane (in $O_2$, 1 L/min) and maintained at 2-3% inhaled isoflurane (in $O_2$, 1 L/min) by nose cone during surgery, depending on the breathing rate and paw pinch response. The backs of the animals were shaved with shaving clippers and the exposed skin was cleaned with 2% chlorohexidine.

For lumbar subpial injections, the skin overlaying the Th8-L1 vertebrae was cut with a scalpel and the paravertebral muscle was detached from Th10-12 spinal vertebrae using scissors. The animal was then mounted into a standard stereotaxic frame using mouse spinal clamps, and both sides of the lamina of the Th10-12 vertebrae were shaved using a dental drill (drill bit: 0.9 mm, speed: 20,000 rpm) until cracks appeared. Cracked bone fragments were removed with forceps and the dorsal surface of the lumbar spinal cord was exposed. The dura was then cut open about 1 cm using a 30G stainless steel needle and forceps.

For cervical subpial injections, the dorsal neck skin was incised 1.5-2.0 cm using scissors to expose the C1-C2 segments. The atlanto-occipital membrane of the *cisterna magna* was then removed using a 23G stainless steel needle and forceps. The incision site was cleaned of any tissue and bone debris using cotton swabs. The dura was then cut open about 1 cm using a 30G stainless steel needle and forceps.

Opening the Pial Membrane and Inserting the Subpial Needle for AAV9 Delivery—

A 34G pia-penetrating needle was mounted into the Z-arm of an XYZ manipulator using a glass capillary holder. The pia-penetrating needle was formed by sharpening the beveled tip of a 34G needle using a glass capillary beveller with a coarse diamond abrasive plate (5.0 µm to 50 µm tip sizes) at a grinding angle of 15-20°. The tip of the needle (1 mm length, measured from the tip) was then gently bent to about 90°. Using a surgical dissecting scope set to 8-10× magnification, the pia was penetrated at an angle of about 5-10° from the tissue surface with the pia-penetrating needle by about 1 mm using the X-arm of the XYZ manipulator. After opening the pia, the pia-penetrating needle was removed horizontally from the subpial space using the X-arm of the XYZ manipulator.

A blunt 36G injection needle was formed by polishing the blunt tip of the needle with a glass capillary beveller with coarse diamond abrasive (5.0 µm to 50 µm tip sizes) to remove sharp edges. The tip of the needle (2-3 mm length, measured from the tip) was then gently bent to about 90°. The injection needle was loaded with AAV9-UBI-GFP virus using a 50-µL microsyringe connected to the injection needle with PE-10 or PE-20 tubing. The needle was then mounted to the Z-arm of a second XYZ manipulator using a glass capillary holder. Manipulating the X, Y, and Z arms of the second manipulator, the tip of the injection needle was positioned into the pia-penetrated site and then advanced about 2-3 mm into the subpial space. The final titers of the AAV9-UBI-GFP were adjusted to $1.2 \times 10^{13}$ genome copies per mL (gc/mL). The AAV9-UBI-GFP (1.5, 3.0, or 5.0 µL) was then injected into the subpial space using a 50 µL syringe (see Table 1 for experimental groups). The injection needle was removed from the subpial space after injection was complete. Thereafter, the muscle and skin were closed using 4.0 monofilament suture and surgical clips. The animals were allowed to recover on a heating pad with pain being controlled by injecting buprenorphine 0.05 mg/kg/sc every 12 h for 2-3 days post-surgery.

TABLE 1

Experimental Groups. All experiments were performed in adult C57BL/6J mice.

| Experimental Groups | Site/level of AAV9 delivery (*) | Volume of AAV9 inj. infusion rate | Survival time | Tissue analysis |
|---|---|---|---|---|
| Group A (n = 7) | C2 (bilateral) | 5 µL/5 min | 14 days | Brain + spinal cord |
| Group B (n = 12) | L1-L2 (bilateral) | 1.5 µL or 3 µL, 60 sec/µL | 14 days | Brain + spinal cord |
| Group C (n = 6) | C2 + L1-L2 (bilateral at each level) | 5 µL/5 min | 14 days | Spinal cord |

*—bilateral = two subpial injections one delivered into the right and one to the left subpial space of injected segments(s) are performed.

At a predetermined time point after the subpial injections, the animals were euthanized and transcardially perfused with 20 mL of heparinized saline followed by 20 mL of 4% paraformaldehyde in PBS. The spinal cords and brains were dissected using a bone rongeur and post-fixed in 4% paraformaldehyde in PBS overnight at 4° C. The spinal cords and brains were cryoprotected with 30% sucrose in PBS for a minimum of 5-7 days. For immunofluorescence staining of spinal cord and brain sections, free-floating sections were incubated in primary antibodies overnight. After incubation, the sections were washed three times in PBS and incubated with fluorescence-conjugated donkey anti-rabbit, donkey anti-chicken, and donkey anti-goat secondary antibodies. The sections where then mounted on microscopy slides and dried at room temperature followed by covering with anti-fade medium. Images were captured using an epifluorescence fluorescence microscope (objectives: 10×, NA-0.3; 20×, NA-0.8; and 63×, NA-1.4).

Potent Transgene Expression in Subpially AAV9-Injected Segments—

Figure 13A:
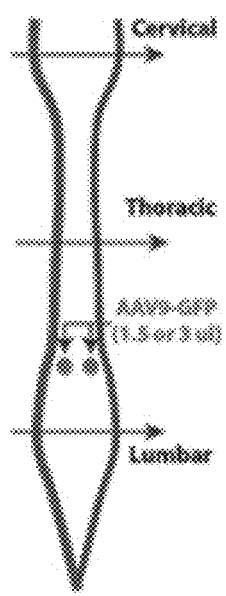
FIGS. 13A-13F are pictorial diagrams showing potent spinal parenchymal GFP expression after lumbar subpial AAV9-UBI-GFP delivery in adult mice.
Figure 13B:
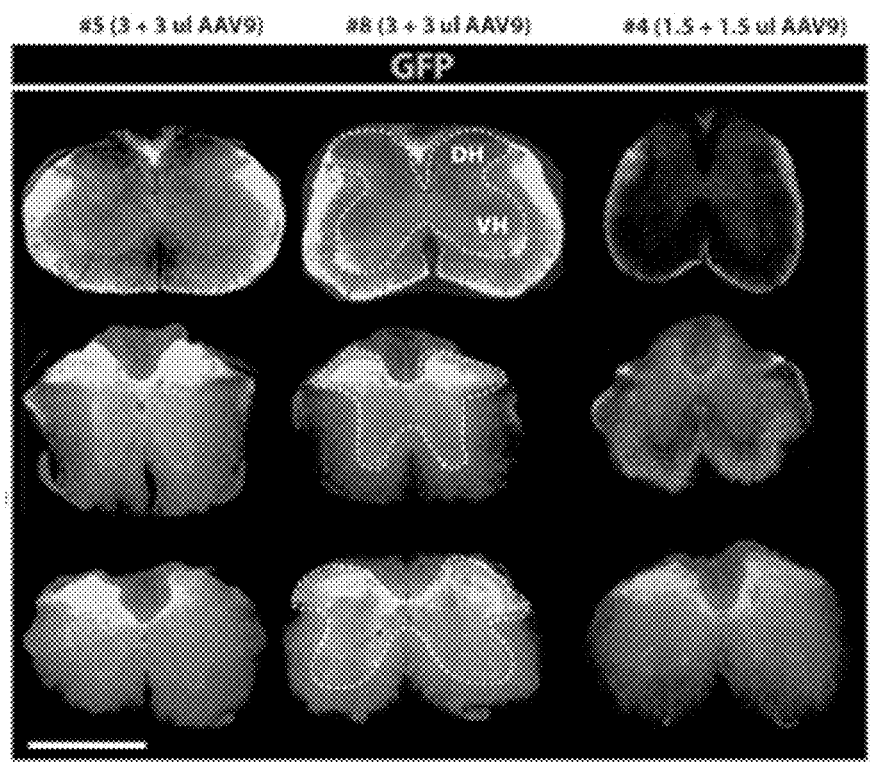
Figure 13C:
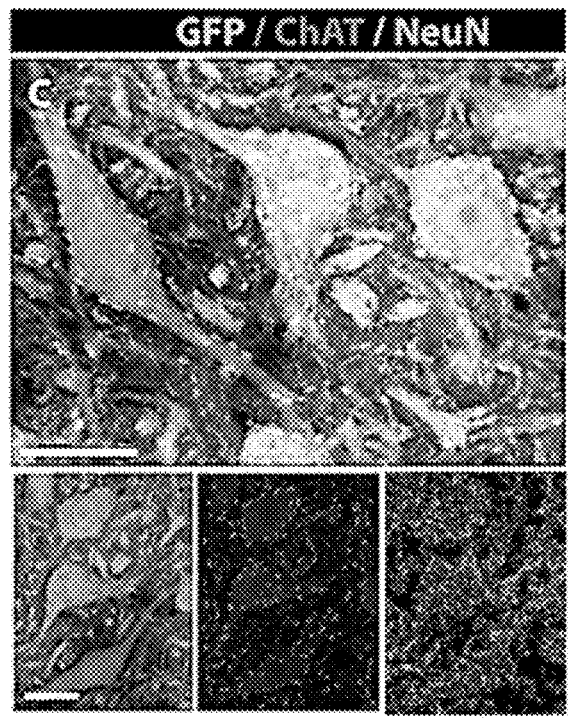
Figure 13D:
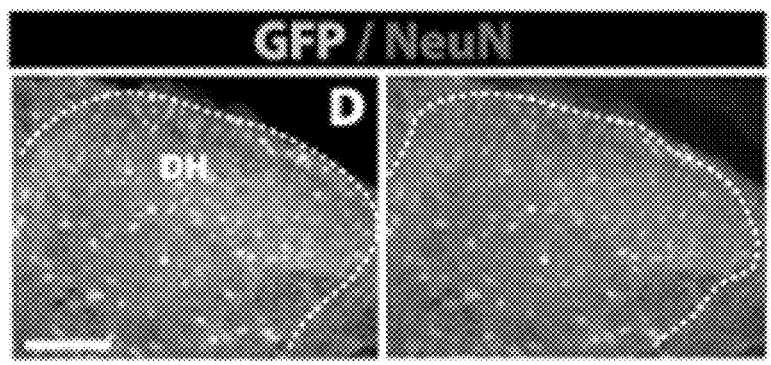
Figure 13E:
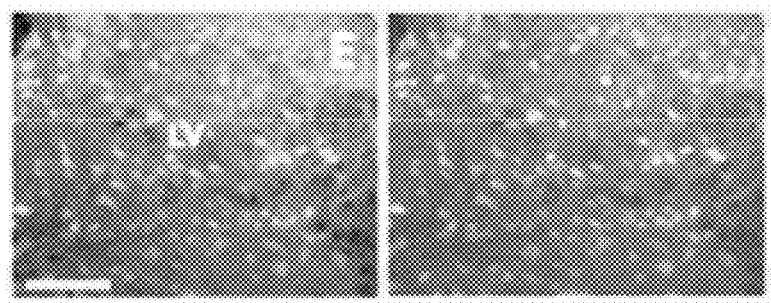
Figure 13F:
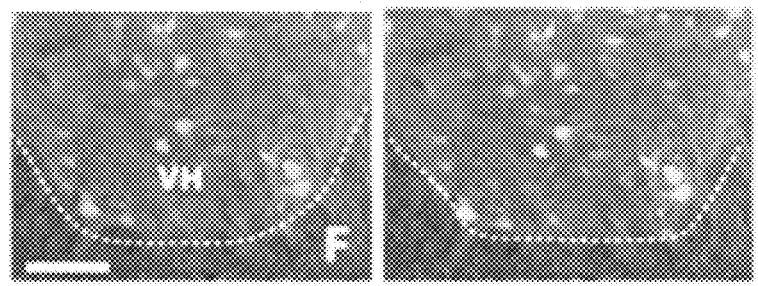
Figures 14A, 14B, 14C, 14D:
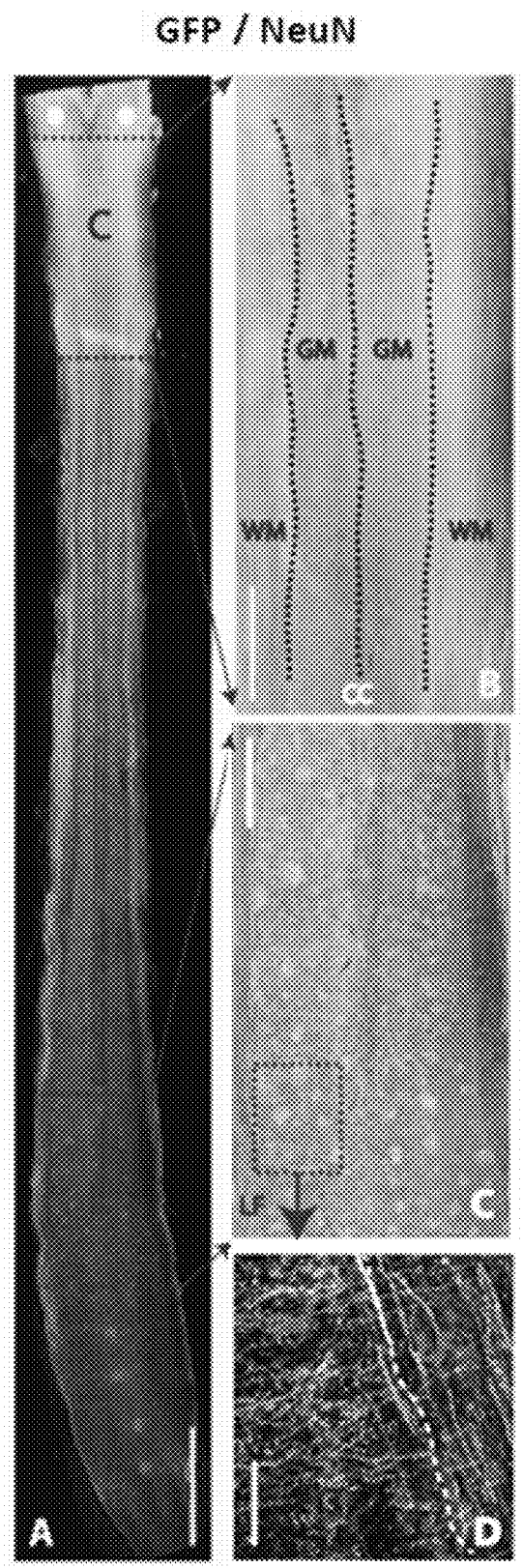

The analysis of transgene (GFP) expression in spinal cord sections at 14 days after AAV9 delivery showed AAV9-dose dependent GFP expression throughout the spinal parenchyma. First, two bilateral 3 µL injections of AAV9-UBI-GFP injected into the upper lumbar subpial space were associated with the near-complete infection of the white and gray matter in the whole lumbar spinal cord, extending to the upper thoracic segments (FIGS. 13A and 13B, left and middle columns). Two bilateral 1.5 µL injections of AAV9-UBI-GFP into the upper lumbar subpial space were associated with a similar near-complete infection of the white and gray matter in the whole lumbar spinal cord (as seen after injections of 3 µL); however, the mid-thoracic segments showed only occasionally infected neurons (FIG. 13B, right column). Staining with α-motoneuronspecific (ChAT) and neuron-specific (NeuN) antibodies showed consistent GFP expression in the entire population of lumbar α-motoneurons (FIG. 13C) and interneurons localized in the dorsal horn (FIG. 13D), intermediate zone (FIG. 13E), and ventral horn (FIG. 13F). Second, two bilateral cervical injections of AAV9 (5 µL for each injection) led to similar GFP expression in the white and gray matter in the whole cervical spinal cord (gray and white matter) and in the upper thoracic segments (FIGS. 14A and 14B). Analysis of lumbar spinal cord sections in the same animals showed a high density of GFP+ descending axons terminating in the vicinity of the lumbar GFP-negative α-motoneurons and interneurons (FIGS. 14C and 14D). The delivery of two bilateral cervical and two bilateral upper lumbar injections of AAV9 (5 µL for each injection) was associated with GFP expression in the entire spinal cord, from the upper cervical to sacral segments, and was homogenously present in the white and gray matter (FIG. 14E-14H).

Retrograde and Anterograde Transport-Mediated Transgene Expression in Supraspinal Motor and Sensory Centers—

Figure 15A:
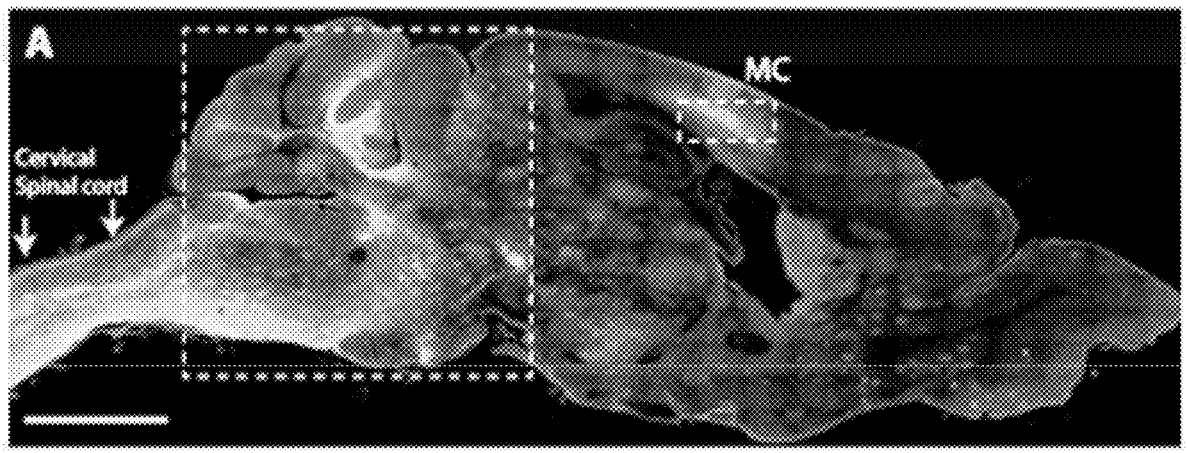
FIGS. 15A-15D are pictorial diagrams showing potent retrograde and anterograde AAV9-UBI-GFP-mediated GFP expression in brain motor and sensory centers.
Figure 15B:
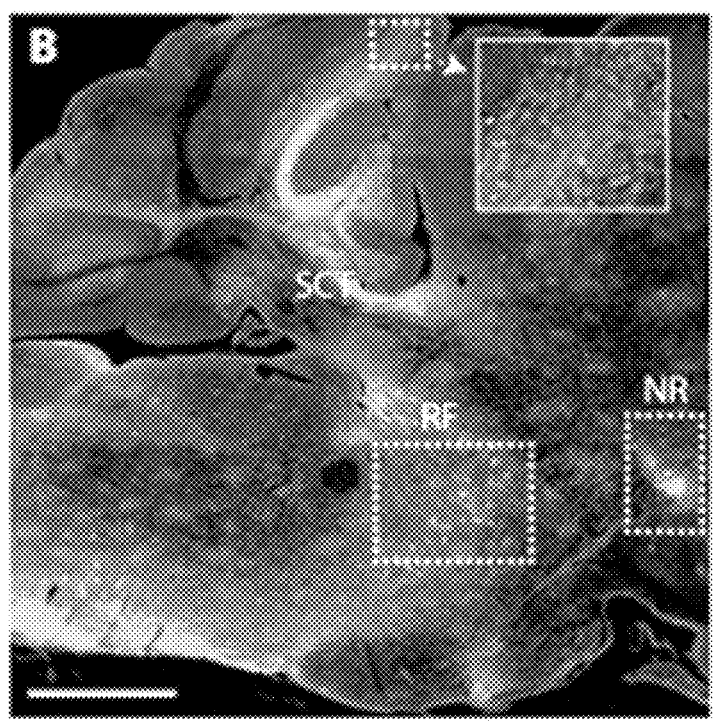
Figure 15C:
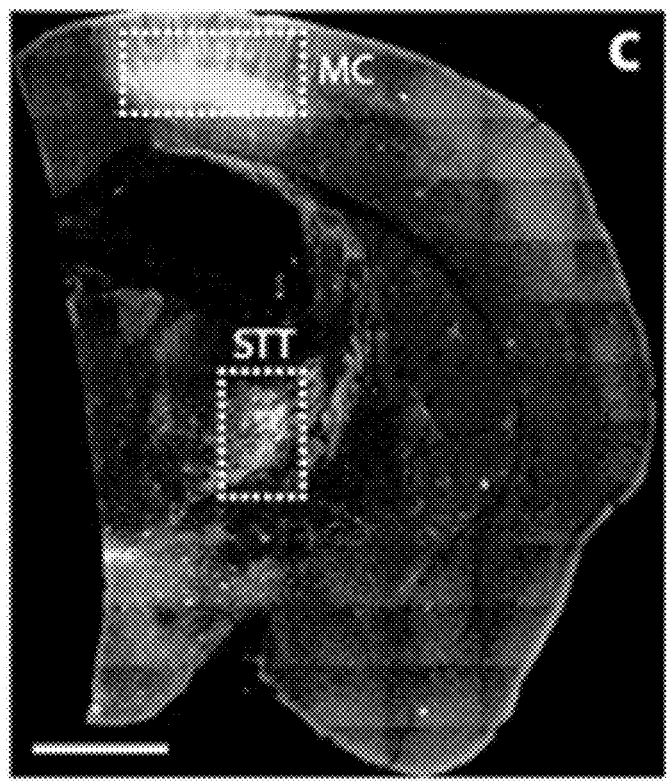
Figure 15D:
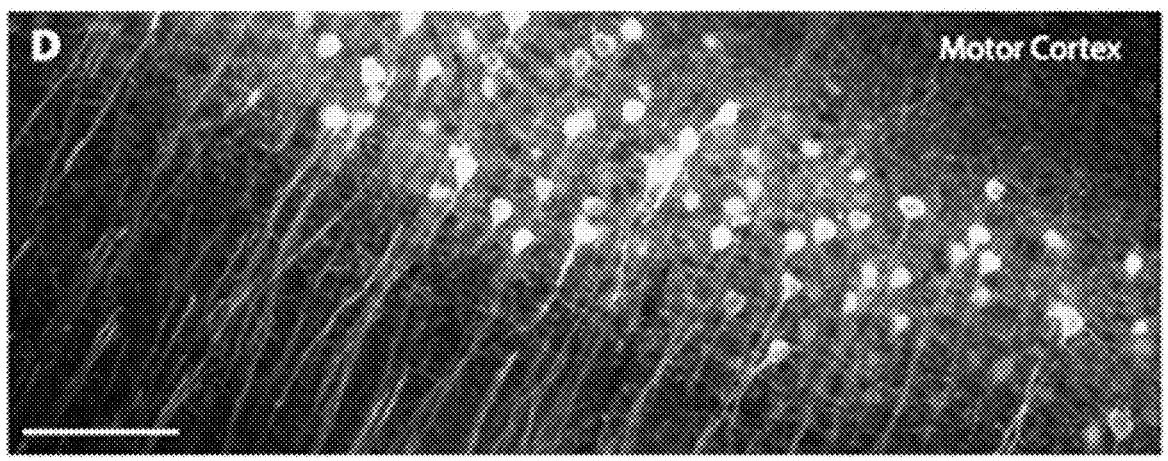

Widespread GFP expression in the lumbar or cervical spinal cord after subpial AAV9 delivery was associated with robust retrograde and anterograde infection-mediated GFP positivity in the supraspinal descending axons and their projecting neurons and in axons and terminals of ascending tracts (FIG. 15A). Thus, intense GFP positivity was seen in neurons localized in the reticular formation (RF), nucleus ruber (NR), and motor cortex (MC) (FIGS. 15B-15D). Similarly, clear GFP immunoreactivity was seen in the terminals of the spinocerebellar (SCT), spinoreticular, and spinothalamic tracts (STT) (FIGS. 15B-15D).

Although the invention has been described with reference to the above example, it will be understood that modifications and variations are encompassed within the spirit and scope of the invention. Accordingly, the invention is limited only by the following claims.

What is claimed is:

1. A method of spinal trans-parenchymal infection of a nucleic acid molecule in a subject comprising administering a nucleic acid molecule to the subpial space of a subject, wherein the step of administering comprises:
    (a) exposing a spinal segment of a vertebra of the subject;
    (b) creating a pial opening within the spinal segment by penetrating the pia with a needle tip of a guide tube at an angle of about 5-10° relative to the pia;
    (c) advancing a catheter through the guide tube into the subpial space; and
    (d) delivering the nucleic acid molecule to the subpial space of the subject.

2. The method of claim 1, wherein the nucleic acid molecule is administered in a mixture containing about 1-10% dextrose.

3. The method of claim 1, wherein the nucleic acid molecule is a vector.

4. The method of claim 3, wherein the vector is a lentiviral vector, adenoviral vector, or an adeno-associated vector.

5. The method of claim 4, wherein the vector is an AAV9 particle.

6. The method of claim 5, wherein the vector comprises a nucleic acid molecule encoding a protein or functional RNA that modulates or treats a neurodegenerative disorder.

7. The method of claim 6, wherein the neurodegenerative disorder is amyotrophic lateral sclerosis (ALS), Huntington's disease, Alzheimer's disease, or Parkinson's disease.

8. The method of claim 1, wherein the nucleic acid molecule is delivered as a single injection.

9. The method of claim 1, further comprising administering one or more second subpial injections of the nucleic acid molecule into a different spinal segment of the vertebra of the subject by repeating steps (a)-(d).

10. The method of claim 1, further comprising administering one or more intrathecal injections of the nucleic acid molecule to the subject.

11. The method of claim 1, wherein the subject is a mammal.

12. The method of claim 11, wherein the subject is human.

13. A method of delivering a nucleic acid molecule to the subpial space of a subject comprising:
 (a) exposing a spinal segment of a vertebra of the subject;
 (b) creating a pial opening within the spinal segment by penetrating the pia with a needle tip of a guide tube at an angle of about 5-10° relative to the pia;
 (c) lifting the penetrated pia with the needle tip of the guide tube;
 (d) advancing a catheter through the guide tube and into subpial space; and
 (e) delivering a composition comprising the nucleic acid molecule through the catheter to the subpial space of the subject.

14. The method of claim 1, further comprising withdrawing the guide tube prior to delivering the nucleic acid molecule to the subpial space of the subject.

15. The method of claim 13, further comprising withdrawing the guide tube prior to delivering the nucleic acid molecule to the subpial space of the subject.

16. The method of claim 1, wherein the needle tip of the guide tube is bent to about 90°.

17. The method of claim 6, wherein the nucleic acid molecule encodes neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TH), GTP-cyclohydrolase (GTPCH), aspartoacylase (ASPA), or amino acid decorboxylase (AADC).

18. The method of claim 6, wherein the nucleic acid molecule encodes a functional RNA that inhibits the expression of SOD1.

19. The method of claim 13, wherein the needle tip of the guide tube is bent to about 90°.

20. The method of claim 13, wherein the nucleic acid molecule encodes a protein or functional RNA that modulates or treats a neurodegenerative disorder.

21. The method of claim 19, wherein the nucleic acid molecule encodes neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TH), GTP-cyclohydrolase (GTPCH), aspartoacylase (ASPA), or amino acid decorboxylase (AADC).

22. The method of claim 19, wherein the nucleic acid molecule encodes a functional RNA that inhibits the expression of SOD1.

* * * * *